(12) United States Patent
Sakuma et al.

(10) Patent No.: US 9,622,955 B2
(45) Date of Patent: Apr. 18, 2017

(54) METHOD OF TREATMENT OR PREVENTION OF HAIR LOSS OR FOR THE ENHANCEMENT OF HAIR GROWTH

(71) Applicant: Advangen International Pty Ltd, Sydney, New South Wales (AU)

(72) Inventors: Sadatoshi Sakuma, Yokohama (JP); Maria Halasz, Sydney (AU); Darren Jones, Avalon (AU)

(73) Assignee: Advangen International Pty Ltd, Sydney (AU)

(*) Notice: Subject to any disclaimer, the term of this patent is extended or adjusted under 35 U.S.C. 154(b) by 85 days.

(21) Appl. No.: 14/464,358

(22) Filed: Aug. 20, 2014

(65) Prior Publication Data

US 2015/0044139 A1 Feb. 12, 2015

Related U.S. Application Data

(63) Continuation of application No. 13/576,747, filed as application No. PCT/AU2011/000194 on Feb. 23, 2011, now abandoned.

(30) Foreign Application Priority Data

Feb. 24, 2010 (AU) ................................ 2010900771

(51) Int. Cl.
| | |
|---|---|
| *A61K 38/18* | (2006.01) |
| *A61K 38/00* | (2006.01) |
| *A61P 17/14* | (2006.01) |
| *A61K 9/00* | (2006.01) |
| *A61K 8/64* | (2006.01) |
| *A61K 49/00* | (2006.01) |
| *A61Q 7/00* | (2006.01) |

(52) U.S. Cl.
CPC ................ *A61K 8/64* (2013.01); *A61K 38/18* (2013.01); *A61K 49/0004* (2013.01); *A61K 49/0008* (2013.01); *A61Q 7/00* (2013.01); *A61K 2800/59* (2013.01)

(58) Field of Classification Search
None
See application file for complete search history.

(56) References Cited

U.S. PATENT DOCUMENTS

2002/0065314 A1* 5/2002 Nielsen ................ A61K 31/275
514/526
2003/0202960 A1 10/2003 Colley

OTHER PUBLICATIONS

Alexandrescu et al., (2009) "The cutaneous epidermal growth factor network: Can it be translated clinically to stimulate hair growth?" Dermatology Online Journal, 15(3):1-9.
Vukicevic et al., (1992) "Identification of Multiple Active Growth Factors in basement Membrane Matrigel Suggests Caution in Interpretation of Cellular Activity Related to Extracellular Matrix Components" Exp. Cell Res. 202, p. 1-8.
Van der Horst, E., et al., (2008) "The Growth Factor Midkine Antagonizes VEGF Signaling in Vitro and In Vivo", Neoplasia, 10(4):340-347.

* cited by examiner

Primary Examiner — Maria Leavitt
Assistant Examiner — Kimberly A Aron
(74) Attorney, Agent, or Firm — Carol L. Francis; Bozicevic, Field & Francis LLP

(57) ABSTRACT

The present application relates to use of a Midkine family protein for growing hair on a mammal, or in the manufacture of a medicament for growing hair on a mammal, especially for treatment or prevention of different forms of alopecia.

10 Claims, 14 Drawing Sheets

(A)

(B)

(C)

(A)

(B)

(C)

(A)

(B)

(C)

(D)

METHOD OF TREATMENT OR PREVENTION OF HAIR LOSS OR FOR THE ENHANCEMENT OF HAIR GROWTH

CROSS-REFERENCE TO RELATED APPLICATION

This application claims the benefit of priority from Australian Application No. 2010900771 filed 24 Feb. 2010, the contents of which are incorporated in their entirety by reference.

FIELD OF THE INVENTION

The present application relates to the filed of therapy and prevention of hair loss or hair thinning in mammals, such as in humans suffering from or having a propensity to develop alopecia, and to the promotion of hair growth in mammals, such as in humans suffering from or having a propensity to develop alopecia.

BACKGROUND TO THE INVENTION

Hair and Hair Development

Hair is integral to our body image and can have a profound influence on our self-esteem and self-confidence. The hair of non-human mammal species is commonly referred to as "fur". Unless specifically stated otherwise, or the context requires otherwise, the term "hair" as used herein shall be taken to include "fur". The term "hair" shall also be taken to include hair on any part of a mammalian body, including the eyebrow, edge of the eyelid, armpit, and inside of the nostril, unless the context requires otherwise. Thus, hair may include head hair, eyebrow hair, eyelash, cilia, or other body hair.

Each hair comprises two structures: the shaft and the follicle. The primary component of the hair shaft is keratin. The hair shaft contains three layers of keratin, however the inner layer i.e., the medulla, may not be present. The middle layer i.e., the cortex, makes up the majority of the hair shaft. The outer layer i.e., the cuticle, is formed by tightly-packed scales in an overlapping structure. Pigment cells are distributed throughout the cortex and medulla giving the hair its characteristic color. The follicle contains several layers. At the base of the follicle is a projection called a papilla, which contains capillaries, or tiny blood vessels, that feed the cells. The living part of the hair, the area surrounding the papilla called the bulb, is the only part fed by the capillaries. The cells in the bulb divide every 23 to 72 hours, faster than any other cells in the body. The follicle is surrounded by an inner root sheath and an outer root sheath. These two sheaths protect and mould the growing hair shaft. The inner root sheath follows the hair shaft and ends below the opening of a sebaceous (oil) gland, which produces sebum, and sometimes an apocrine (scent) gland. The outer root sheath continues all the way up to the sebaceous gland. An erector pili muscle attaches below the sebaceous gland to a fibrous layer around the outer sheath. When this muscle contracts; it causes the hair to stand up.

Human skin comprises two types of hair: vellus hair and terminal hair. Vellus hair is short, fine, "peach fuzz" body hair. It is a very soft, generally pale, and short hair that grows in most places on the human body in both sexes. Venus hair is generally less than two centimeters in length, and the follicles from which vellus hair grows are not connected to sebaceous glands. It is observed most easily in those having less terminal hair to obscure it, such as women and children. It also is found in pre-adolescents and in males exhibiting male-pattern baldness. Terminal or "androgenic" hair is developed hair, which is generally longer, coarser, thicker and darker than vellus hair. Phases of growth in terminal hair are also more apparent than in vellus hair, by virtue of a generally-longer anagen phase. Terminal hair has associated sebaceous glands. In puberty, some vellus hair may develop into terminal hair. Under other conditions, such as male pattern baldness, terminal hair may revert to a vellus-like state There are three sequential stages of hair growth: catagen, telogen, and anagen. Anagen is the active growth phase of the hair during which the cells in the root of the hair are dividing rapidly. Anagen hairs are anchored deeply into the subcutaneous fat and cannot be pulled out easily. When a new hair is formed, it pushes the club hair up the follicle, and eventually out. During this phase, the hair grows about 1 cm every 28 days. Scalp hair stays in this active phase of growth for 2-6 years. Human subjects that have difficulty growing their hair beyond a certain length may have a shortened anagen phase, whereas those having an ability to grow longer hair quickly may have a longer anagen phase. In humans, the hair on the arms, legs, eyelashes, and eyebrows generally has a short anagen compared to head or scalp hair. The catagen phase is a transitional stage that lasts for about 2-3 weeks in humans, during which time growth stops, thereby forming "club" hair. Telogen is a resting phase, lasting for about 100 days for scalp hair and much longer for other body hair. During telogen, the hair follicle is at rest, the club hair is formed, and compared to hair in anagen, the hair in telogen is located higher in the skin and can be pulled out readily. The root of telogen hair comprises a visible solid, hard, dry, and white material. Shedding of telogen hair is normal, and up to 75 hairs in telogen are shed from the human scalp daily. The shed hairs are normally replaced as about the same number of follicles enter anagen daily. At any time in normal scalp, approximately 80% to 90% of follicles are in anagen, about 1% to 3% are in catagen i.e., undergoing involution, and about 5% to 10% are in telogen.

Conditions of Hair Loss and/or Reduced Hair Growth

Hair loss or hair thinning includes any condition that results in a reduced ability to replace shed hairs or that results in enhanced shedding without their concomitant or subsequent replacement e.g., brittle hair growth, thin hair growth, short hair growth, sparse hair growth, alopecia, or hair de-pigmentation. For example, the hair cycle can become uncontrolled leading to accelerated hair loss, which may be temporary or permanent. As used herein, the term "alopecia" is used to refer to hair loss, unless specifically stated otherwise or the context requires otherwise.

Alopecia can have various causes. Hereditary androgenic alopecia is the commonest form of alopecia: it is manifested by a decrease in hair volume, or even baldness, and affects up to about 70% of men. Acute alopecia may be associated with treatment by chemotherapy, stress, severe malnutrition, iron deficiency, hormonal disorders, AIDS, or acute irradiation. Alopecia areata, which seems to be of auto-immune origin (mechanism of cellular mediation), is characterized by "patches" of varying size in one or more body places. Alopecia totalis refers to a form of alopecia areata that extends over the entire scalp, and alopecia universalis refers to a form of alopecia areata that extending over the whole body. Mechanistically, in all forms of alopecia, hair loss is directly-related to a reduced ability, slowing or failure of the follicle to enter the anagen phase, or a failure to maintain the follicle in the anagen phase, such that formation of a hair shaft reduces, is slowed or ceases altogether. Hair may move into the catagen phase before sufficient growth is achieved in the anagen phase, thus becoming in a sustained manner short and thin (i.e. "hair thinning"). Chemotherapeutic agents, radiotherapeutic agents, and other medicinal products may induce necrosis or apoptosis of the follicle as a side-effect of the therapy, also preventing the follicle to enter anagen. For example, alkylating agents e.g., temozolomide, busulfan, ifosamide, melphalan hydrochloride, carmustine, lomustine or cyclophosphamide, and antimetabolites e.g., 5-fluorouracil, capecitabine, gemcitabine, floxuridine, decitabine, mercaptopurine, pemetrexed disodium, methotrexate or dacarbazine, and natural products e.g., vincristine, vinblastine, vinorelbine tartrate, paclitaxel, docetaxel, ixabepilone, daunorubicin, epirubicin, doxorubicin, idarubicin, mitoxantrone, mitomycin, dactinomycin, irinotecan, topotecan, etoposide, teniposide, etoposide phosphate, or bleomycin sulfate, and biologics e.g., filgrastim, pegfilgrastim, bevacizumab, sargramostim or panitumumab, and hormones or hormone-related agents e.g., megestrol acetate, fluoxymesterone, leuprolide, octreotide acetate, tamoxifen citrate or fluxymesterone, and other therapeutic agents e.g., sorafenib, erlotinib, oxaliplatin, dexrazoxane, anagrelide, isotretinoin, bexarotene, vorinostat, adriamycin, cytoxan, taxol, leucovorin, oxaliplatin, and combinations of the foregoing agents are known to induce temporary or permanent alopecia.

Alopecia caused by any of the foregoing factors is a source of low self-esteem and anxiety for many patients. For those undergoing chemotherapy or radiation therapy for cancer, alopecia adds to discomfort from other adverse side-effects of the therapy e.g., nausea, skin rash, etc. Many alopecia sufferers, including patients receiving chemotherapy, choose to use wigs, hair pieces, scarves, hats or turbans to cover their bald or thinning regions. Those suffering from hair loss often experience embarrassment and fear being ridiculed by others because they look different. Some may take to wearing oversized eyeglasses in an attempt to hide the absence of eyelashes and/or eyebrows. In some subjects, alopecia may lead to depression.

Animal Models of Alopecia

There are several useful models of alopecia in humans, that have been acknowledged in the art for use in testing efficacy of alopecia remedies and other hair growth-promoting therapies.

For example, the stumptailed macaque possesses hereditary balding characteristics similar in many respects to that of androgenic alopecia in humans, is used to obtain a morphometric assessment of the rate of cyclic change of the hair follicle, including rates of cyclic progression (resting to regrowing phase, and regrowing to late anagen phase) and overall changes in follicular size. These primates are also reasonably good predictors of compound efficacy, and for example, have been employed to test efficacy of minoxidil on androgenic alopecia. Cessation of topical minoxidil treatment resulted in a renewal of the balding process, with folliculograms demonstrating increases in the proportion of resting follicles. This withdrawal from treatment apparently had no effect on hair regrowth during subsequent reapplications of minoxidil. Such treatment resulted in regrowth similar to that in the first treatment phase. Continuous treatment of topical minoxidil for 4 years has not resulted in systemic or local side effects in these animals. See e.g., Brigham et al., *Clin. Dermatol.* 6, 177-187, 1998; Sundberg et al., *Exp. Mol. Pathol.* 67, 118-130 (1999), the contents of which are incorporated herein by reference in their entirety).

Collectively, the findings obtained from studies on mouse models support the concept of alopecia areata as an autoimmune disease, and several rodent models with spontaneous and induced alopecia areata have been identified. For example, the Dundee Experimental Bald Rat (DEBR) was the first rodent model validated that developed spontaneous alopecia areata and is utilized to identify candidate alopecia areata susceptibility gene loci (Michie et al., *Br J Dermatol.*, 125, 94-100, 1991, incorporated herein by reference). The most extensively-characterized and readily-accessible alopecia areata model is the C3H/HeJ mouse model (Sundberg et al., *J Invest Dermatol.*, 102, 847-56, 1994, incorporated herein by reference). Aging C3H/HeJ mice (females at 3-5 months of age or older and males at more than 6 months of age) develop histopathological and immunohistochemical features of human alopecia areata. Alopecia develops diffusely or in circular areas on the dorsal surface of sufficiently-aged animals. Histologically, the changes in this non-scarring alopecia appear limited to anagen follicles surrounded by mononuclear cells composed primarily of cytotoxic or cytostatic (CD8+) and helper (CD4+) T cells, this is associated with follicular and hair shaft dystrophy. Pedigree tracing of affected C3H/HeJ mice suggests that this non-scarring alopecia may be an inherited and complex polygenic disease with a female predominance at younger ages. C3H/HeJ mice with alopecia areata can be used to study the efficacy of current treatments of alopecia areata, to study the effectiveness and safety profile of new treatment forms in established alopecia areata, and to assess the influence of various factors on the development of alopecia areata in order to prevent the onset of the disease.

Paus et al., *Am. J. Pathol.* 144, 719-734 (1994) have also described a rodent model of acute alopecia, the entire content of which is incorporated herein by reference. In this model, alopecia is induced by a single intraperitoneal injection of cyclophosphamide to C57 BL/6 mice. In depilated C57 BL/6 mice, the hair follicles are synchronized to anagen. By day 9 after depilation, all follicles are mature anagen VI follicles, and the skin is characterized by grey-to-black coloured hair shafts. Histologically, macroscopically, and functionally, depilation-induced anagen VI follicles are indistinguishable from spontaneously-developing anagen follicles. Around day 16 after depilation, follicle regression occurs without loss of hair shafts in the depilated animals, and skin colour converts from black to pink, indicating both induction of catagen and cessation of melanogenesis. The development of catagen follicles is indicated macroscopically by a change in skin color from black to light grey, and occurs in large waves appearing in the neck region first and then the flanks and tail regions. At day 20 after depilation, all follicles enter telogen again, characterized by change in skin color from grey to pink. When cyclophosphamide is administered to C57 BL/6 mice on day 9 after depilation, the animals show rapid and reproducible visible signs of acute alopecia dose-dependent, including significant loss of fur and premature termination of anagen characterized by depigmentation leading to a grey skin appearance by day 12-14. Thus, follicles of the neck region are generally in catagen 3-5 days after cyclophosphamide treatment. Hair shafts on the backs of animals are also removed easily by rubbing at days 12-14, and by day 15, as much as 60% of the dorsal surface may be exhibit alopecia. The color change and alopecia induced by cyclophosphamide reflect the induction of dystrophic forms of anagen and catagen in anagen VI follicles. In cyclophosphamide-treated animals, follicles also progress to telogen rapidly, as evidenced by pink skin, and rapid loss of fur due to damage of the hair follicle. Telogen is shortened following cyclophosphamide treatment, and normal telogen hair follicles enter the next hair cycle, so that animals develop new hair shafts on days 16-20 i.e., within about 7-10 days following treatment. These new hair shafts are often de-pigmented due to the presence of dystrophic anagen follicles that have not had time to produce new, normally-pigmented hair shafts. Later, pigmented hair shafts develop.

Therapy for Conditions of Hair Loss and/or Reduced Hair Growth

Existing therapies for alopecia include topical minoxidil and derivatives thereof e.g., U.S. Pat. Nos. 4,139,619 and 4,596,812, and European Pat. Nos. EP-0353123, EP-0356271, EP-0408442, EP-0522964, EP-0420707, EP-0459890 and EP-0519819, spironolactone, cyproterone acetate, flutamide, finasteride, progesterone or estrogen. Anti-androgen agents such as finasteride and minoxidil are known for treating androgenic alopecia. None of these treatments is broadly applicable. For example, such treatments may not prevent hair loss during treatment with a chemotherapeutic agent. On the other hand, such compounds may produce undesirable side-effects. For example, minoxidil is a potent vasodilator. Patients may also require frequent dosing with such compounds to achieve an effective outcome. For example, minoxidil provides very transient effects, because cessation of topical minoxidil treatment results generally in a renewal of the balding process, with folliculograms demonstrating increases in the proportion of resting follicles. Minoxidil is also recommended for administration twice-daily at 2% concentration. Notwithstanding that finasteride provides an advance over minoxidil in being deliverable orally, and is considered to be the best treatment available, about 35% or more of balding male recipients show poor or no response to that drug. Finasteride may also produce significant side-effects for some users, as a number of male users have reported erectile dysfunction, impotence, low libido, or gynecomestica after using that drug. In those males suffering such side-effects, the side effects may not disappear after ceasing finasteride.

Various prostaglandin analogs have also been disclosed for use in treatment of androgenic alopecia e.g., travoprost, voprostol, and these may also require frequent administration e.g., at least daily, however single dosages of travoprost have been described e.g., U.S. Pat. Publication 20100190853. Prostaglandin analogs are also known for use in treatment of alopecia associated with chemotherapy e.g., U.S. Pat. Publication 20110002286. Prostaglandin analogs may have a variety of adverse effects e.g., muscular constriction mediating inflammation, calcium movement, hormone regulation and cell growth control.

Midkine Family Proteins

Midkine (MK) is a growth/differentiation factor that was first discovered as a gene product expressed transiently in the process of differentiation induction of embryonic tumor cells (EC) with retinoic acid. MK is known to produce a broad range of adverse and beneficial biological effects. The expression of MK is increased in human cancer cells, including esophageal cancer, thyroid cancer, urinary bladder cancer, colorectal cancer, gastric cancer, pancreatic cancer, chest cancer, liver cancer, lung cancer, breast cancer, neuroblastoma, neuroblastoma, glioblastoma, uterine cancer, ovarian cancer, and Wilms' tumor, and is believed to promote the survival and migration of cancer cells and to facilitate neovascularization. MK is also known to promote the migration of inflammatory cells such as macrophages and neutrophil, leading to inflammation. MK is also known to stimulate the proliferation of cultured endometrial interstitial cells during endometriosis. Thus, MK inhibitors e.g., antibodies, aptamers or RNAi targeting MK protein or RNA, have been disclosed for use in treatment of a broad range of inflammatory diseases such as arthritis, autoimmune disease, rheumatic arthritis, osteoarthritis, multiple sclerosis, postoperative adhesion, inflammatory colitis, psoriasis, lupus, asthma, neutrophil functional abnormalities, and endometriosis.

Beneficial effects of MK are also known, wherein MK is also involved in promoting the formation of nascent intima following blood vessel damage and the onset of nephritis in an ischemic event, and in reducing postoperative adhesions in rheumatic subjects. Thus, MK protein has been disclosed for use in treatment of cerebral ischemia, cardiac ischemia, restenosis following vascular reconstruction surgery, cardiac coronary arterial vascular obstructive disease, cerebral vascular obstructive disease, renal vascular obstructive disease, peripheral vascular obstructive disease, and arteriosclerosis.

Pleiotrophin (PTN or HB-GAM) is a midkine family protein having approximately 50% identity at the amino acid sequence level to MK. Both MK and PTN comprise a high content of cysteine and basic residues. All the 10 cysteine residues are conserved in MK and PTN, and structurally, both can be divided into the N-domain and the C-domain. As a result of NMR analysis, it is known that these two molecules have very similar three-dimensional structures. Each domain consists of three β sheets, connected via a flexible linker region. K79, R81, and K102, considered to be important to the binding of to chondroitin sulfate and heparin, are conserved between the two proteins. MK and PTN also share three-dimensional structures wherein these basic residues appear in the vicinity of the protein surface. Accordingly, PTN has been disclosed previously for the same medical indications as MK.

It is to be understood that, if any prior art publication is referred to herein, such reference does not constitute an admission that the publication forms a part of the common general knowledge or background art in Australia or elsewhere.

SUMMARY OF THE INVENTION

In work leading up to the present invention, the inventor sought to develop protein-based reagents, e.g., for topical administration to a subject, that enhance hair growth or the initiation of hair growth in subjects that are susceptible to hair loss or suffer hair loss. The inventor also sought to develop an effective topical protein-based formulation that can be applied readily to the skin and exert an effect notwithstanding the barrier that the dermis generally provides to external agents.

The inventor developed an animal model of hair loss consisting essentially of an aged mouse that suffers hair loss e.g., in the form of bald regions or alopecic sites. The inventor found that topical application of midkine or pleotrophin protein to the animal model induced hair growth or the recommencement of hair growth in these bald regions or alopecic sites. Topical formulations of midkine or pleiotrophin were found to be superior to parenteral formulations in producing these hair growth promoting effects in this animal model.

The data provided herein also show that, in contrast to minoxidil, midkine and pleiotrophin failed to stimulate hair growth visibly in healthy animals that have been shaved to synchronize their follicle in anagen, and exhibited no clinical symptoms of alopecia. This suggests that midkine and pleiotrophin may act by a more specific mechanism than minoxidil that does not comprise a vasodilatory effect of the dermal papillae. Thus, fur regrowth stimulated by a midkine family protein may arise from an anti-apoptotic effect of midkine on follicles to thereby extend their anagen phase, or alternatively, or the re-entry of normal telogen follicles into the next hair cycle.

In further work leading to the present invention, the applicant utilized the accepted animal model of chemotherapy-induced alopecia (CIA) described e.g., by Paus et al., *Am. J. Pathol.* 144, 719-734 (1994), the contents of which are incorporated herein in their entirety. The applicant performed a randomised trial in which all animals were shaved and waxed, and five groups of animals were administered daily with a topical formulation of midkine protein for 7 days before and 19 days following i/p injection of cyclophosphamide, and another two groups of animals were administered daily with a topical formulation of midkine protein for 19 days following i/p injection of cyclophosphamide. Control mice received a saline placebo. Data presented herein indicate that topical administration of a midkine family protein e.g., MK and/or PTN, before chemotherapy, or before and after chemotherapy, significantly reduces the severity of fur loss i.e., promotes fur growth at all time points following administration of the chemotherapeutic agent. Treatment with a midkine family protein also retains a greater proportion of follicles in anagen following treatment with cyclophosphamide, as evidenced by more animals having black or dark grey skin when treated with midkine family protein than for the group receiving a placebo. This suggests an anti-apoptotic effect on anagen follicles. These beneficial effects are detectable in the period immediate following chemotherapy when follicles have not yet recovered, and during later follicle recovery after chemotherapy has ceased. Data presented herein also indicate that topical administration of a midkine family protein e.g., MK and/or PTN, following chemotherapy at least improves recovery of follicles, as demonstrated by a reduced incidence of alopecia compared to subjects receiving a placebo. Thus, animals treated daily with topical midkine protein following chemotherapy also lose less hair in total than animals not receiving treatment, and the reduced hair loss is nearly as effective as in animals treated with midkine protein before and after chemotherapy. Subjects receiving midkine therapy before or after chemotherapy also exhibit a higher rate of hair growth during the follicle recovery period, suggesting an anti-apoptotic effect of midkine on follicles to thereby extend their anagen phase, or alternatively, enhanced re-entry of normal telogen follicles into the next hair cycle following treatment with midkine.

It is to be understood that the methods described herein for the aged mouse model of hair loss are transferable to testing in other animal models of alopecia of humans, including the stump-tailed macaque 21-23 model of androgenic alopecia and/or the hairless (hr/hr) model of papular atrichia, as described herein.

The data provided herein therefore support the use of compositions comprising a midkine family protein in promoting hair growth and/or reducing hair loss and/or reducing hair thinning and/or preventing hair loss and/or preventing hair thinning and/or delaying hair loss and/or delaying hair thinning e.g., in aging subjects, subjects suffering from alopecia such as androgenic alopecia or acute alopecia. Typically, effective compositions of the invention for treatment and/or prevention of alopecia are formulated for topical administration, however parenteral formulations may also be employed, such as for co-administration with a cytotoxic or cytostatic agent of acute alopecia that is generally administered parenterally e.g., a chemotherapeutic agent.

Accordingly, one example of the present invention provides a formulation e.g., a topical formulation, comprising an amount of a midkine family protein, such as midkine, pleiotrophin or a variant or homolog of midkine or pleiotrophin, and a topical carrier, excipient or emollient, effective to prevent hair loss and/or promote hair growth and/or enhance hair growth. By "topical formulation" is meant that the formulation is capable of being applied externally to the dermis of a mammal, or is applied to the dermis. For example, the formulation may be useful for administration to the dermis or skin of a male subject who is susceptible to hair loss or at risk of hair loss, such as a subject suffering from or at risk of developing male-pattern baldness. In another example, the formulation of the invention is useful for administration to the dermis or skin of a subject suffering from a disease or condition associated with hair loss e.g., alopecia, especially acute alopecia or androgenic alopecia.

In one example, the topical formulation comprises an amount of a midkine family protein and a topical carrier, excipient or emollient effective to treat or prevent hair loss and/or promote hair growth and/or enhance hair growth. Preferably, the formulation is for administration to the dermis or skin of a subject who is susceptible to hair loss or at risk of hair loss, or for administration to the dermis or skin of a subject suffering from hair loss. It will be appreciated that the topical formulation is suitable for treatment or prevention of alopecia e.g., an acute form of alopecia or androgenic alopecia. For example, the formulation may be used for treatment or prevention of alopecia in a subject undergoing treatment with a cytotoxic agent or cytostatic agent or to whom treatment with a cytotoxic agent or cytostatic agent has been prescribed. The midkine family protein may be midkine, pleiotrophin, midkine-like protein, or a truncated midkine protein.

The present invention thus provides improved topical formulations comprising a therapeutically-effective amount of a midkine family protein e.g., an effective amount of a midkine protein or pleiotrophin protein or biologically-active variant thereof to enhance hair growth. The topical formulations of the invention are particularly useful for the prevention or treatment of alopecia, including androgenic alopecia, acute alopecia, alopecia areata, alopecia totalis and alopecia universalis. The topical formulations of the invention are preferably for treatment of androgenic alopecia. The topical formulations of the invention are even more preferably for the treatment of acute alopecia in subjects undergoing therapy with a cytotoxic or cytostatic compound that causes hair loss, especially a chemotherapeutic agent, radiotherapeutic agent, or antiviral compound such as administered to a subject infected with HIV-1. The topical formulations of the invention are also preferably for the prevention of acute alopecia in subjects about to undergo therapy with a cytotoxic or cytostatic compound that causes hair loss, especially a chemotherapeutic agent, radiotherapeutic agent, or antiviral compound such as administered to a subject infected with HIV-1.

It is to be understood that the topical formulations of the invention are useful for the stimulation of hair growth in subjects suffering from or having a predisposition to develop androgenic alopecia or male pattern baldness, and/or in subjects about to undergo therapy with a cytotoxic or cytostatic compound that causes hair loss, or undergoing such therapy.

It is also to be understood that the topical formulations of the present invention are compatible with various types of therapeutic agents or carriers with which they are combinable or capable of being administered sequentially or simultaneously or concomitantly. For example a topical formulation-comprising a midkine family protein may further comprise a second compound for treatment of the same condition and/or be co-administered with such second compound(s). In such circumstances, the efficacy of the midkine family protein is supplemented by the action of the second compound. For example, the midkine family protein is co-administered with cestradiol and/or oxandrolone and/or minoxidil and/or finasteride or an agent that blocks the conversion of testosterone to dihydrotesterone. Alternatively, or in addition, the topical formulation of the invention is co-administered with a cytotoxic or cytostatic compound that causes hair loss e.g., in the case of a subject undergoing chemotherapy or radiation therapy or treatment for HIV-1 infection or AIDS, such circumstances, the efficacy of the midkine family protein counteracts the hair-loss effect of the cytotoxic or cytostatic compound.

Another example of the present invention provides for the use of a midkine family protein in the manufacture of a medicament e.g., a topical medicament for preventing and/or treating hair loss in a subject suffering from alopecia or having a propensity to develop alopecia. The medicament may be for administration to a section of the population that is susceptible to hair loss or suffers from hair loss, such as a subject suffering from or at risk of developing male-pattern baldness. For example, the subject may have no visible symptoms of alopecia, however suffers from a genetic condition that predisposes the subject to alopecia, or the subject may be about to undergo therapy with a cytotoxic or cytostatic agent or antiviral compound that induces alopecia. In another example, the topical medicament is useful for administration to the dermis or skin of a subject suffering from a disease or condition associated with hair loss e.g., alopecia. For example, the subject may have a pre-existing alopecia or be undergoing therapy with a cytotoxic or cytostatic agent or antiviral compound that induces alopecia whether or not visible symptoms of alopecia have developed before midkine family protein therapy is commenced. The midkine family protein is especially useful in manufacture of a medicament for treatment or prevention of acute alopecia in a subject undergoing chemotherapy, and such a medicament may be formulated for administration by a topical or parenteral route, however topical formulations are preferred.

By "topical medicament" is meant that the active agent i.e., midkine family protein, such as midkine, pleiotrophin or a variant or homolog of midkine or pleiotrophin, is formulated with a topical carrier, excipient or emollient for application to the dermis of a mammal.

In one particularly preferred example, the use of a midkine family protein is in the manufacture of a medicament for treatment or prevention of alopecia, e.g., an acute form of alopecia or androgenic alopecia, in a human or other mammalian subject. The subject may be a human or mammalian subject a subject undergoing treatment with a cytotoxic agent or cytostatic agent or to whom treatment with a cytotoxic agent or cytostatic agent has been prescribed. The medicament may be a formulation for topical application. The midkine family protein may be midkine, pleiotrophin, midkine-like protein, or a truncated midkine protein.

Another example of the present invention provides a method of treatment or prevention of hair loss, said method comprising administering to a subject in need thereof e.g., a subject suffering from alopecia or having a propensity to develop alopecia, a formulation, e.g., a topical formulation, comprising an amount of a midkine family protein, such as midkine, pleiotrophin or a variant or homolog of midkine or pleiotrophin, and a topical carrier, excipient or emollient, effective to prevent hair loss and/or promote hair growth and/or enhance hair growth on the subject. The subject will generally be a mammal such as a human. For example, the method of the invention is useful for the treatment of male subjects who are susceptible to or at risk of hair loss such as in male-pattern baldness. Such subjects may have no visible symptoms of alopecia, however suffers from a genetic condition that predisposes the subject to alopecia, or the subject may be about to undergo therapy or be undergoing therapy with a cytotoxic or cytostatic agent or antiviral compound, that induces alopecia. In another example, the method of the invention is useful for the treatment of a subject suffering from a disease or condition associated with hair loss e.g., alopecia. Such subjects may have a pre-existing alopecia or be undergoing therapy with a cytotoxic or cytostatic agent or antiviral compound that induces alopecia wherein symptoms of alopecia have developed. The treatment and prevention of subjects undergoing chemotherapy or to whom chemotherapy has been prescribed is clearly encompassed by the inventive method.

Another example of the present invention provides a method of promoting or enhancing hair growth or hair initiation, such as during or following therapy with a cytotoxic or cytostatic agent or antiviral compound that induces alopecia, said method comprising administering to a subject in need thereof a formulation e.g., a topical formulation comprising an amount of a midkine family protein, such as midkine, pleiotrophin or a variant or homolog of midkine or pleiotrophin, and a topical carrier, excipient or emollient, effective to prevent hair loss and/or promote hair growth and/or enhance hair growth on the subject.

In another example, the present invention provides a method of treatment or prevention of hair loss, said method comprising administering to a subject in need thereof, e.g., a subject suffering from alopecia such as an acute form of alopecia or androgenic alopecia or susceptible to developing said alopecia, a formulation comprising an amount of a midkine family protein and a carrier, excipient or emollient, effective to prevent hair loss and/or promote hair growth and/or enhance hair growth on the subject. Preferably, the formulation is a topical formulation and said method comprises administering the topical formulation to an affected area of the skin of the subject in which hair has been lost or to an area of skin from which hair is likely to be lost. The formulation may be administered to a subject suffering from alopecia for a time and under conditions sufficient to reduce hair loss and/or effect hair growth in the subject. Alternatively, or in addition, formulation may be administered to a subject suffering from alopecia for a time and under conditions sufficient to prevent or reduce apoptosis of follicles of the subject. Alternatively, or in addition, formulation may be administered to a subject suffering from alopecia for a time and under conditions sufficient to extend an anagen phase of follicles of the subject. Alternatively, or in addition, formulation may be administered to a subject suffering from alopecia for a time and under conditions sufficient to promote or advance entry of normal telogen follicles of the subject into a following hair cycle. The method according to the invention is particularly useful for subjects undergoing treatment with a cytotoxic agent or cytostatic agent or to whom treatment with a cytotoxic agent or cytostatic agent has been prescribed. In a preferred example, the midkine family protein may be midkine, pleiotrophin, midkine-like protein, or a truncated midkine protein.

In another example, the invention provides a method of promoting or enhancing hair growth or hair initiation in a subject suffering from hair loss, said method comprising administering to the subject a topical formulation comprising an amount of a midkine family protein and a topical carrier, excipient or emollient effective to prevent hair loss and/or promote hair growth and/or enhance hair growth on the subject. Preferably, the midkine family protein is midkine or pleiotrophin.

In another example, the invention provides a method of reducing hair loss in a subject undergoing chemotherapy or to whom chemotherapy has been prescribed, said method comprising administering to the subject a formulation comprising an amount of a midkine family protein and a carrier, excipient or emollient for a time and under conditions sufficient to prevent or reduce hair loss due to the chemotherapy. Preferably, the method comprises administering the formulation topically to a subject that has been treated with the chemotherapy or to whom chemotherapy has been prescribed before commencement of the chemotherapy. In one example, the method comprises administering the formulation topically to a subject to whom chemotherapy has been prescribed before and after commencement of the chemotherapy. As exemplified herein, the midkine family protein may be midkine.

Another example of the present invention provides an animal model of hair loss consisting essentially of an aged mouse that suffers hair loss e.g., in the form of bald regions or alopecic sites. The present invention clearly extends to the use of this animal model to screen for novel therapeutic and prophylactic compositions of matter that prevent hair loss and/or promote hair growth and/or enhance hair growth, wherein said screen comprises administering a test compound to the animal and determining hair growth and/or reduced hair loss and wherein reduced hair loss and/or increased hair growth and/or an initiation of hair growth on the animal in the presence of the test compound relative to in the absence of the test compound is indicative of the test compound preventing hair loss and/or promoting hair growth and/or enhancing hair growth. In one example of this screening method, the activity of the test compound is compared to the activity of a midkine family protein and a test compound having comparable or enhanced activity relative to the midkine family protein is identified and/or isolated and/or formulated for topical administration in a method of the invention according to any example hereof.

In another example, the present invention provides a method of identifying or isolating a compound that prevents hair loss and/or promotes hair growth and/or enhances hair growth, wherein said method comprises administering a test compound to a mouse, said mouse being aged more than one year and suffering hair loss and having a knockout of one allele of a gene encoding a midkine protein and one other functional allele of the gene, and then determining hair growth and/or reduced hair loss on the mouse, and wherein reduced hair loss and/or increased hair growth and/or an initiation of hair growth on the mouse in the presence of the test compound relative to in the absence of the test compound is indicative of the test compound preventing hair loss and/or promoting hair growth and/or enhancing hair growth.

Definitions

This specification contains nucleotide and amino acid sequence information prepared using PatentIn Version 3.6, presented herein after the claims. Each nucleotide sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:" followed by the sequence identifier (e.g. SEQ ID NO: 1 refers to the sequence in the sequence listing designated as <400>1).

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", is understood to imply the inclusion of a stated step or element or integer or group of steps or elements or integers but not the exclusion of any other step or element or integer or group of elements or integers.

The term "hair" means any hair or fur on the body of a mammal including a human, and includes, for example, head hair, eyebrows, eyelashes, moustaches, beards, chest hair, back hair, arm hair, leg hair, genital hair, nasal hair or ear hair.

As used herein, the term "treat" or "treating" or "treatment" shall be taken to include therapeutic treatment of a pre-existing condition, or prophylactic or preventative measures, wherein the aim is to prevent, ameliorate, reduce or slow down (lessen) hair thinning, hair loss or alopecia. It follows that hair growth, or treatment of hair thinning, refers to normalization of thinned hair, such as in alopecia, and/or increasing the length and thickness of hair. A mammal in need of treatment may already have the condition, or may be prone to have the condition or may be in whom the condition is to be prevented. Such treatment preferably involves an anti-apoptotic effect on follicles to thereby extend their anagen phase, or alternatively, or the re-entry of normal telogen follicles into the next hair cycle.

"Preventing", "prevention", "preventative" or "prophylactic" refers to keeping from occurring, or to hinder, defend from, or protect from the occurrence of a condition, disease, disorder, or phenotype, including an abnormality or symptom. A mammal in need of prevention may be prone to develop the condition.

The term "ameliorate" or "amelioration" refers to a decrease, reduction or elimination of a condition, disease, disorder, or phenotype, including an abnormality or symptom.

The term "therapeutically effective amount" refers to an amount of the Midkine family protein capable of reducing hair thinning, hair loss or alopecia in a mammal to a level which is beneficial to treat or prevent hair thinning, hair loss or alopecia. A therapeutically effective amount may be determined empirically and in a routine manner in relation to treating hair thinning, hair loss or alopecia.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example unless specifically stated otherwise.

Each definition or clarifying term described herein shall be taken to apply mutatis mutandis to each and every example of the invention unless the context requires otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

BRIEF DESCRIPTION OF THE SEQUENCE LISTING

Figure 1:
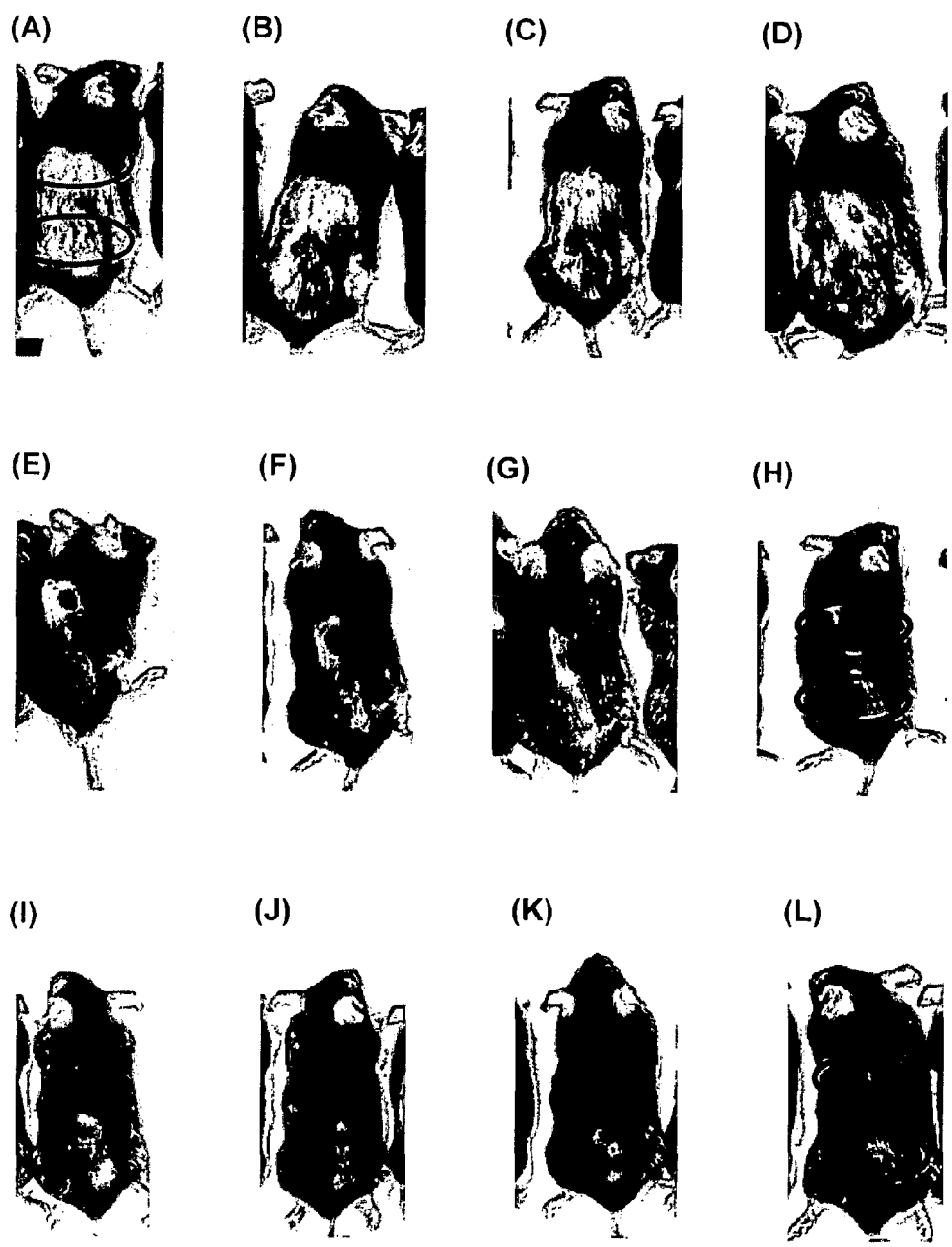
FIG. 1 provides photographic representations showing a fur growth promoting effect of thrice-weekly administration for 15 days of topical formulations comprising midkine (MK) in 40% glycerol (1 µg/ml) or 10 µl of pleiotrophin (PTN) in 40% glycerol (1 µg/ml) to different alopecic regions of alopecic Black 6 MK heterozygous knockout (+/−) mice at 1.5 years of age. In the drawing, the circles in each row indicate the positioning of dermal patches of MK (circle nearer the neck region) and PTN (circles nearer the tail) for each animal in the same row. Panel A shows an animal on the day treatment was commenced. Panels B-L show mice at day 1, 4, 6, 8, 11, 13, 15, 18, 20, 22, and 25 respectively from commencement of treatment. Data indicate that animals treated with a topical formulation of MK or PTN show significant fur regrowth in this animal model, and that fur regrowth occurs more rapidly using MK than PTN. After 15 days when treatment ceased (panel H), MK had an ongoing beneficial effect to day 25. Fur regrowth is not entirely localized to the treated region, since animals showed improved fur condition over their entire dorsal region following treatment.

SEQ ID NO: 1 provides the amino acid sequence of human midkine (Accession identifiers gi|4505135 and ref|NP_002382.1).

SEQ ID NO: 2 provides the amino acid sequence of human pleiotrophin (Accession identifiers gi|4506281 and ref|NP_002816.1).

SEQ ID NO: 3 provides the amino acid sequence of a human midkine-like protein corresponding with SEQ ID NO: 4 of WO 2004/052928).

SEQ ID NO: 4 provides the nucleotide sequence of Human midkine mRNA (Accession identifiers gi|182650 and gb|M69148.1).

DETAILED DESCRIPTION OF THE INVENTION

Midkine Family Protein

Midkine is a 13-kDa protein, which was discovered as a product from a gene whose expression is induced in an early stage of lung tumour cell differentiation due to retinoic acid. Pleiotrophin was discovered in the brain of a newborn rat as heparin-binding protein with an ability of enhancing neurite extension.

As used herein a "Midkine family protein" is a protein that exhibits a similar amino acid sequence to midkine or a functional region thereof and exhibits the same function as or a similar function to that of midkine. A Midkine family protein includes a functional variant of a Midkine family protein.

Even a protein with low identity with midkine may be a Midkine family protein, provided that the protein has the same function as or a similar function to that of midkine. An example of such a Midkine family protein may be midkine (e.g. SEQ ID NO: 1), midkine-like protein (e.g. SEQ ID NO: 3 (WO 2004/052928)), truncated midkine protein, or pleiotrophin (e.g. SEQ ID NO: 2). The Midkine family protein may be a functional variant of a Midkine family protein, including a functional variant of midkine, midkine-like protein, truncated midkine protein, or pleiotrophin. The functional variant may be modified by substitution, deletion, or addition of one or more amino acids relative to the non-modified protein. The functional variant of the Midkine family protein will exhibit a function of midkine.

In one embodiment, the Midkine family protein is midkine. In another embodiment, the Midkine family protein is pleiotrophin.

The function of midkine may be a function of enhancing cell proliferation, inhibiting apoptosis, binding to heparin, enhancing cell migration, or inducing cell differentiation. In one embodiment, the function of MK is inhibiting apoptosis.

"Functional variant" and "variant" as used herein includes either natural protein variants or artificially modified protein variants that exhibit a function of midkine.

As used herein, "modified" or "modification" includes substitution, addition, and/or deletion of an amino acid residue.

The Midkine family protein may have an amino acid sequence that is at least 60%, at least 65%, at least 70%, at least 75%, at least 80%, at least 85%, at least 90%, at least 95%, at least 96%, at least 97%, at least 98%, at least 99% or is 100% identical over its length or functional region to a segment (preferably a continuous segment) of a wild-type Midkine family protein (e.g. any one of SEQ ID NOs: 1 to 3).

A Midkine family protein may comprise 1, 2, 3, 4, 5, 6, 7, 8, 9, or 10, or even 15, 20, 25, 30, 35, 40, 45, or 50 modifications e.g., at selected positions to maintain or enhance midkine function.

Thus, the specifically stated Midkine family protein sequences can vary, provided individual substitution, deletion and/or addition of an amino acid does not strongly impair the function of the Midkine family protein.

The Midkine family protein or their functional variants can also be linked with other peptides or polypeptides or with further chemical groups such as glycosyl groups, lipids, phosphates, acetyl groups or the like, provided they do not strongly adversely influence their midkine function. Thus, the modified Midkine family protein may be a fusion construct. For example, the Midkine family protein may be fused to a peptidyl moiety comprising an art-recognized protein translocation domain to facilitate entry of the Midkine family protein to the follicular cells.

In addition to naturally occurring amino acids, non-naturally occurring amino acids, or modified amino acids, are also contemplated and within the scope of the invention. In fact, as used herein, "amino acid" refers to naturally occurring amino acids, non-naturally occurring amino acids, and amino acid analogs, and to the D or L stereoisomers of each.

Natural amino acids include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), valine (V), hydroxyproline (O and/or Hyp), isodityrosine (IDT), and di-isodityrosine (di-IDT). Hydroxyproline, isodityrosine, and di-isodityrosine are formed post-translationally. In some embodiments, the natural amino acids, in particular the 20 genetically encoded amino acids, are used.

The substitutions may be conservative amino acid substitutions, in which the substituted amino acid has similar structural or chemical properties with the corresponding amino acid in the reference sequence. Alternatively, the substitutions may be non-conservative amino acid substitutions.

By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

Functional variants may be obtained in which the Midkine family protein has been chemically modified at the level of amino acid side chains, of amino acid chirality, and/or of the peptide backbone. These alterations are intended to provide proteins having similar or improved therapeutic properties.

Modifications providing increased potency, prolonged activity, ease of purification, and/or increased half-life will be known to the person skilled in the art.

Functional variants of the Midkine family protein may be identified by modifying the sequence of the protein and then assaying the resulting protein for the ability to function similarly to midkine, for example enhancing cell proliferation, inhibiting apoptosis, binding to heparin, enhancing cell migration, or inducing cell differentiation.

The Midkine family protein can be made by synthetic chemistry of recombinant DNA mutagenesis techniques that are well known to persons skilled in the art. For example, midkine may be produced in accordance with a method disclosed in the Examples of JP-A-H09-95454.

Formulations

The Midkine family protein may be formulated in any form used in the pharmaceutical, quasi-drug, or cosmetic field, preferably suitable for topical administration. For example, the composition may be a hair-growing product, hair or scalp cosmetic (e.g. shampoo, hair conditioner, scalp lotion, scalp cream, hair tonic, etc.), skincare product (e.g. lotion, cream, face cream, face lotion, milk, pack, liquid facial wash, soap, etc.), body care product (e.g. body cream, body lotion, soap, liquid wash, bath additive, etc.), UV protective agent (e.g. sun block, sunscreen lotion, tanning oil, etc.), or cosmetic (e.g. eyeliner, eyebrow pencil, cream, lotion, etc).

Conveniently, the Midkine family protein may be formulated for parenteral administration e.g., with one or more chemotherapeutic drugs, such as by intravenous injection.

Excipients will typically be included in the dosage form e.g., to improve solubility and/or bioadhesion. Suitable excipients include solvents, co-solvents, emulsifiers, plasticizers, surfactants, thickeners, pH modifiers, emollients, antioxidants, and chelating agents, wetting agents, and water absorbing agents. Formulations may also include one or more additives, for example, dyes, colored pigments, pearlescent agents, deodorizers, and odor maskers.

Diluents or fillers increase the bulk of a solid dosage form so that a practical size is provided for compression of tablets or formation of beads and granules. Suitable diluents include, but are not limited to dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Formulations may also comprise one or more dispersants e.g., phosphate-buffered saline (PBS), saline, glucose, sodium lauryl sulfate (SLS), polyvinylpyrrolidone (PVP), polyethylene glycol (PEG), and hydroxypropylmethylcellulose (HPMC).

Formulations may also comprise one or more binders to impart cohesive qualities to a solid dosage formulation, and thus ensure that a tablet, bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose ("HPMC"), microcrystalline cellulose ("MCC"), hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone (PVP).

Formulations may also comprise one or more lubricants to facilitate manufacture or ingestion of a solid dosage unit e.g., a tablet. Examples of suitable lubricants include, but are not limited to, magnesium stearate, calcium stearate, stearic acid, glycerol behenate, polyethylene glycol, talc, and mineral oil.

Formulations may also comprise one or more disintegrants to facilitate dosage form disintegration after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP.

Formulations may also comprise one or more stabilizers and/or preservatives (e.g., E216, E218, and chlorobutanol hemihydrate) to inhibit or retard drug decomposition reactions e.g., by oxidation or bacterial action.

Formulations may also comprise one or more surfactants. Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-00 monolaurate, polyoxyethylene monolaurate, polysorbates, polyoxyethylene octylphenylether, PEG-1000 cetyl ether, polyoxyethylene tridecyl ether, polypropylene glycol butyl ether, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

If desired, solid formulations e.g., tablets, beads, granules, or particles may also contain an amount of a non-toxic auxiliary substance such as a wetting or emulsifying agent, dye, or pH buffering agent.

Pharmaceutical formulations may be presented in unit dose forms containing a predetermined amount of active agent i.e., Midkine family protein, or a derivative or analog thereof, per unit dose. The concentration of active agent may vary depending upon whether or not the formulation is for prevention or therapy, the route of administration, half-life of the compound following administration by the selected route, and the age, weight and condition of the patient including e.g., the severity of problem drinking being treated. For example a unit dose may comprise about 1 µg to 10 ug, or 0.01 mg to 1000 mg, or 0.1 mg to 250 mg, of Midkine family protein, or a derivative or analog thereof. In another example, Midkine family protein, or a derivative or analog thereof may be formulated such that the concentration of active agent is at least about 1% (w/w) or at least about 5% (w/w) or at least about 10% (w/w) or at least about 25% (w/w) based on the total weight of the pharmaceutical composition.

To prepare pharmaceutical formulations, one or more Midkine family proteins is/are mixed with a pharmaceutically acceptable carrier or excipient for example, by mixing with physiologically acceptable carriers, excipients, or stabilizers in the form of, e.g., lyophilized powders, slurries, aqueous solutions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

The amount of the Midkine family protein in a formulation for treatment of alopecia may vary depending on various parameters such as age, sex, and condition of the mammal being treated. For example, the Midkine family protein may be formulated to produce a final concentration of 0.001 to 50% (w/w), 0.001 to 10% (w/w), 0.001 to 5% (w/w), or 0.001 to 1% of the total weight of the medicament. The concentration of the Midkine family protein in a liquid formulation may be, for example, 0.0001 µg/ml to 2 mg/ml, 0.001 µg/ml to 1 mg/ml, 0.01 µg/ml to 500 µg/ml, 0.1 µg/ml to 100 µg/ml, 0.1 µg/ml to 50 µg/ml, 0.1 µg/ml to 10 µg/ml, or 1 µg/ml to 2 µg/ml.

A formulation comprising a midkine family protein and a pharmaceutically acceptable carrier or diluent may further comprise one or adjunctive therapeutic agents for treatment of the same condition, wherein the adjunctive therapeutic agent is suitable for administration by the same route as the midkine family protein(s). For example, a midkine family protein may be formulated for topical administration with cestradiol and/or oxandrolone and/or minoxidil. The adjunctive therapeutic agent is generally present in the formulation at a concentration in accordance with its known prescribed level. The skilled artisan will appreciate that such compositions may provide enhanced therapeutic benefit to the patient, and may be more than additive in their effect.

Formulation of a pharmaceutical compound will vary according to the route of administration selected (e.g., solution, emulsion, capsule). For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, Remington's Pharmaceutical Sciences, 17th Edition, Mack Publishing Co., Pa., 1985). For inhalation, the agent can be solubilized and loaded into a suitable dispenser for administration (e.g., an atomizer, nebulizer or pressurized aerosol dispenser).

Pharmaceutical formulations can be adapted for administration by any appropriate route, for example by the oral (including buccal or sublingual), topical (including buccal, sublingual or transdermal), or parenteral (including subcutaneous, intramuscular, intravenous or intradermal) route. Such formulations can be prepared by any method known in the art of pharmacy, for example by bringing into association the active ingredient with the carrier(s), diluent(s) or excipient(s).

For example, the Midkine family protein is formulated for topical administration. Topical compositions include those pharmaceutical forms in which the Midkine family protein(s) is(are) applied externally by direct contact with the skin surface to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures thereof.

For topical use on the eyelids or eyebrows, the active Midkine family protein(s) can be formulated in aqueous alcohol solutions, creams, ointments or oils exhibiting physiologically acceptable osmolarity by addition of pharmacologically acceptable buffers and salts. Such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid etc. as additives. Furthermore, particularly aqueous solutions may contain viscosity increasing agents such as polysaccharides, e.g., methylcellulose, mucopolysaccharides, e.g., hyaluronic acid and chondroitin sulfate, or polyalcohol, e.g., polyvinylalcohol. Various slow releasing gels and matrices may also be employed as well as soluble and insoluble ocular inserts, for instance, based on substances forming in-situ gels. Depending on the actual formulation and Midkine family protein(s) to be used, various amounts of the drug and different dose regimens may be employed.

For topical use on the skin and the scalp, the Midkine family protein(s) can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used.

In another example, a formulation comprising one or more Midkine family proteins is adapted for parenteral administration e.g., by subcutaneous or intravenous injection. Such formulations include aqueous and non-aqueous sterile injection solutions which may contain the antioxidants as well as buffers, bacteriostats and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets. In one example, one or more Midkine family proteins is formulated as an intravenous lipid emulsion or a surfactant micelle or polymeric micelle (see., e.g., Jones et al., *Eur. J. Pharmaceutics Biopharmaceutics* 48, 101-111, 1999; Torchilin *J. Clin, release* 73, 137-172, 2001 for parenteral administration.

Sustained release injectable formulations are produced e.g., by encapsulating one or more Midkine family proteins in porous microparticles comprising a pharmaceutical agent and a matrix material having a volume average diameter between about 1 μm and 150 μm, e.g., between about 5 μm and 25 μm diameter. In one example, the porous microparticles have an average porosity between about 5% and 90% by volume. In another example, the porous microparticles further comprise one or more surfactants, such as a phospholipid. The microparticles may be dispersed in a pharmaceutically acceptable aqueous or non-aqueous vehicle for injection. Suitable matrix materials for such formulations comprise a biocompatible synthetic polymer, a lipid, a hydrophobic molecule, or a combination thereof. For example, the synthetic polymer can comprise, for example, a polymer selected from the group consisting of poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co -caprolactone), copolymers, derivatives and blends thereof. In a preferred example, the synthetic polymer comprises a poly(lactic acid), a poly(glycolic acid), a poly(lactic-co-glycolic acid), or a poly(lactide-co-glycolide).

In another example, pharmaceutical formulations are adapted for oral administration e.g., as capsules, soft gels, or tablets; powders or granules, solutions or suspensions in aqueous or non-aqueous liquids, edible foams or whips, or oil-in-water liquid emulsions or water-in-oil liquid emulsions. An oral formulation may comprise an intragranular phase comprising an effective amount of a Midkine family protein and at least one carbohydrate alcohol and an aqueous binder. The pharmaceutical formulation may be substantially lactose-free. Preferred carbohydrate alcohols for such formulations are selected from the group consisting of mannitol, maltitol, sorbitol, lactitol, erythritol and xylitol. Preferably, the carbohydrate alcohol is present at a concentration of about 15% to about 90%. A preferred aqueous binder is selected from the group consisting of hydroxypropyl cellulose, hydroxypropyl methylcellulose, carboxymethyl cellulose sodium, polyvinyl pyrrolidones, starches, gelatins and the like. A binder is generally present in the range of from about 1% to about 15% by weight. The intragranular phase can also comprise one or more diluents, such as, for example, a diluent selected from the group consisting of microcrystalline cellulose, powdered cellulose, calcium phosphate-dibasic, calcium sulfate, dextrates, dextrins, alginates and dextrose excipients. Such diluents are also present in the range of about 15% to about 90% by weight. The intragranular phase can also comprise one or more disintegrants, such as, for example, a disintegrant selected from the group consisting of a low substituted hydroxypropyl cellulose, carboxymethyl cellulose, calcium carboxymethylcellulose, sodium carboxymethyl cellulose, sodium starch glycollate, crospovidone, croscarmellose sodium, starch, crystalline cellulose, hydroxypropyl starch, and partially pregelatinized starch. A disintegrant is generally present in the range of from about 5% to about 20% by weight. Such a formulation can also comprise one or more lubricants such as, for example, a lubricant selected from the group consisting of talc, magnesium stearate, stearic acid, hydrogenated vegetable oils, glyceryl behenate, polyethylene glycols and derivatives thereof, sodium lauryl sulphate and sodium stearyl fumarate. A lubricant is generally present in the range of from about 0.5% to about 5% by weight. Such formulations are made into a tablet, capsule, or soft gel e.g., by a process comprising mixing a Midkine family protein and at least one carbohydrate alcohol to form a dry blend, wet granulating the dry blend with an aqueous binder so as to obtain an intragranular phase, and further formulating the resulting intragranular phase so as to provide the formulation. Typically, tablet or capsules is prepared to contain an appropriate unit dosage e.g., from 0.001 mg to 1000 mg.

Alternatively, a liquid or semi-solid pharmaceutical formulation for oral administration e.g., a hard gel or soft gel capsule comprising one or more Midkine family proteins may be prepared. The formulation may comprise a first carrier component and optional second carrier component, which carriers comprise, independently, one or more of lauroyl macrogel glycerides, caprylocaproyl macrogel glycerides, stearoyl macrogel glycerides, linoleoyl macrogel glycerides, oleoyl macrogel, glycerides, polyalkylene glycol, polyethylene glycol, polypropylene glycol, polyoxyethylene-polyoxypropylene copolymer, fatty alcohol, polyoxyethylene fatty alcohol ether, fatty acid, polyethoxylated fatty acid ester, propylene glycol fatty acid ester, fatty ester, glycerides of fatty acid, polyoxyethylene-glycerol fatty ester, polyoxypropylene-glycerol fatty ester, polyglycolized glycerides, polyglycerol fatty acid ester, sorbitan ester, polyethoxylated sorbitan ester, polyethoxylated cholesterol, polyethoxylated castor oil, polyethoxylated sterol, lecithin, glycerol, sorbic acid, sorbitol, or polyethoxylated vegetable oil.

The formulation may also comprise an emulsifying/solubilizing component comprising one or more of metallic alkyl sulfate, quaternary ammonium compounds, salts of fatty acids, sulfosuccinates, taurates, amino acids, lauroyl macrogol glycerides, caprylocaproyl macrogolglycerides, stearoyl macrogel glycerides, linoleoyl macrogel glycerides, oleoyl macrogel glycerides, polyalkylene glycol, polyethylene glycol, polypropylene glycol, polyoxyethylene-polyoxypropylene copolymer, polyoxyethylene fatty alcohol ether, fatty acid, polyethoxylated fatty acid ester, propylene glycol fatty acid ester, polyoxyethylene-glycerol fatty ester, polyglycolized glycerides, polyglycerol fatty acid ester, sorbitan ester, polyethoxylated sorbitan ester, polyethoxylated cholesterol, polyethoxylated castor oil, polyethoxylated sterol, lecithin, or polyethoxylated vegetable oil.

The formulation may also comprise an anti-crystallization/solubilizing component which, when present, generally comprises one or more of metallic alkyl sulfate, polyvinylpyrrolidone, lauroyl macrogol glycerides, caprylocaproyl macrogolglycerides, stearoyl macrogol glycerides, linoleoyl macrogol glycerides, oleoyl macrogol glycerides, polyalkylene glycol, polyethylene glycol, polypropylene glycol, polyoxyethylene-polyoxypropylene copolymer, fatty alcohol, polyoxyethylene fatty alcohol ether, fatty acid, polyethoxylated fatty acid ester, propylene glycol fatty acid ester, fatty ester, glycerides of fatty acid, polyoxyethylene-glycerol fatty ester, polyglycolized glycerides, polyglycerol fatty acid ester, sorbitan ester, polyethoxylated sorbitan ester, polyethoxylated cholesterol, polyethoxylated castor oil, polyethoxylated sterol, lecithin, or polyethoxylated vegetable oil.

A Midkine family protein may be formulated with a hydrophobic polymer; preferably a bioadhesive polymer and optionally encapsulated in or dispersed throughout a microparticle or nanoparticle. The bioadhesive polymer improves gastrointestinal retention via adherence of the formulation to the walls of the gastrointestinal tract. Suitable bioadhesive polymers include polylactic acid, polystyrene, poly(bis carboxy phenoxy propane-co-sebacic anhydride) (20:80) (poly (CCP:SA)), alginate (freshly prepared); and poly(fumaric anhydride-co-sebacic anhydride (20:80) (poly (FA:SA)), types A (containing sudan red dye) and B (undyed). Other high-adhesion polymers include p(FA:SA) (50:50) and non-water-soluble polyacrylates and polyacrylamides. Preferred bioadhesive polymers are typically hydrophobic enough to be non-water-soluble, but contain a sufficient amount of exposed surface carboxyl groups to promote adhesion e.g., non-water-soluble polyacrylates and polymethacrylates; polymers of hydroxy acids, such as polylactide and polyglycolide; polyanhydrides; polyorthoesters; blends comprising these polymers; and copolymers comprising the monomers of these polymers. Preferred biopolymers are bioerodable, with preferred molecular weights ranging from 1000 to 15,000 kDa, and most preferably 2000 to 5000 Da. Polyanhydrides e.g., polyadipic anhydride ("p(AA)"), polyfumaric anhydride, polysebacic anhydride, polymaleic anhydride, polymalic anhydride, polyphthalic anhydride, polyisophthalic anhydride, polyaspartic anhydride, polyterephthalic anhydride, polyisophthalic anhydride, poly carboxyphenoxypropane anhydride and copolymers with other polyanhydrides at different mole ratios, are particularly preferred. Blends of hydrophilic polymers and bioadhesive hydrophobic polymers can also be employed. Suitable hydrophilic polymers include e.g., hydroxypropylmethylcellulose, hydroxypropylcellulose, carboxymethylcellulose, polyvinylalcohols, polyvinylpyrolidones, and polyethylene glycols. Other mucoadhesive polymers include DOPA-maleic anhydride co polymer, isopthalic anhydride polymer, DOPA-methacrylate polymers, DOPA-cellulosic based polymers, and DOPA-acrylic acid polymers.

Alternatively, the Midkine family protein may be encapsulated or molecularly dispersed for oral administration in a polymer to reduce particle size and increase dissolution. The polymers may include polyesters such as poly(lactic acid) or P(LA), polycaprylactone, polylactide-coglycolide or P(LGA), poly hydroxybutyrate poly β-malic acid); polyanhydrides such as poly(adipic)anhydride or P(AA), poly (fumaric-co-sebacic)anhydride or P(FA:SA), poly(sebacic) anhydride or P(SA); cellulosic polymers such as ethylcellulose, cellulose acetate, cellulose acetate phthalate, etc; acrylate and methacrylate polymers such as Eudragit RS 100, RL 100, E100 PO, L100-55, L100, S100 (distributed by Rohm America) or other polymers commonly used for encapsulation for pharmaceutical purposes and known to those skilled in the art. Also suitable are hydrophobic polymers such as polyimides. Blending or copolymerization sufficient to provide a certain amount of hydrophilic character can be useful to improve wetability of the materials. For example, about 5% to about 20% of monomers may be hydrophilic monomers. Hydrophilic polymers such as hydroxylpropylcellulose (HPC), hydroxpropylmethylcellulose (HPMC), carboxymethylcellulose (CMC) are commonly used for this purpose.

Oral formulations may be "immediate release" formulations e.g., that release at least 85% (wt/wt) of the Midkine family protein within 60 minutes in vitro. Alternatively, the formulation may be a "controlled release" formulation that releases drug more slowly than an immediate release formulation i.e., it takes longer than 60 minutes to release at least 85% (wt/wt) of the drug in vitro. To extend the time period for release, the ratio of active agent to polymer can be increased. Increased relative drug concentration is believed to have the effect of increasing the effective compound domain size within the polymer matrix thereby slowing dissolution. In the case of a polymer matrix containing certain types of hydrophobic polymers, the polymer will act as a mucoadhesive material and increase the retention time of the active compound in the gastrointestinal tract. Increased drug dissolution rates combined with the mucoadhesive properties of the polymer matrix increase uptake of the active compound and reduce differences found in the fed and fasted states for the compounds.

The compositions described herein may further comprise components which are generally used in cosmetics, for example, oils, detergents, UV absorbers, alcohols, chelating agents, pH modifiers, preservatives, thickeners, pigments, fragrances, and skin nutritional supplements. Specifically, the composition may comprise active ingredients used for skin cosmetics, such as zinc oxide microparticles, titanium oxide, UV absorbers such as Parsol MCX and Parsol 1789, vitamins such as ascorbic acid, moisturising agents such as hyaluronate sodium, petrolatum, glycerin, and urea, hormonal agents, skin-lightening agents such as kojic acid, arbutin, placenta extract, and rucinol, steroid drugs, inhibitors of production or release of a chemical mediator such as arachidonic metabolite and histamine (e.g. indometacin and ibuprofen), anti-inflammatory drugs such as receptor antagonist, anti-androgenic agents, sebum secretion suppressing agents such as vitamin A acid, royal jelly extract, and royal jelly acid, peripheral blood-vessel dilators such as tocopherol nicotinate, alprostadil, isoxsuprine hydrochloride, and tolazoline hydrochloride, carbon dioxide with peripheral blood-vessel dilating activity, blood circulation promoting agents such as minoxidil, carpronium chloride, capsicum tincture, vitamin E variants, ginkgo extract, and Swertia japonica extract, cellular stimulants such as pentadecanoic acid glyceride and nicotinic-aid amide, antimicrobials such as hinokitiol, L-menthol, and isopropylmethylphenol, glycyrrhizinic acid and variants or salts thereof, ceramide and ceramide analogs.

Dosage Units and Frequency of Administration

The dose and frequency of the Midkine family protein or the medicament may be appropriately modified depending on the situation.

In general, the Midkine family protein, or the medicament comprising the Midkine family protein(s), may be used with any frequency. Typically, the Midkine family protein(s) are applied repeatedly for a sustained period of time topically on the part of the body to be treated, for example, the eyelids, eyebrows, skin or scalp. The preferred dosage regimen will generally involve regular, such as daily, weekly, twice-weekly, or thrice-weekly, administration for a period of treatment of at least one about one month, more preferably at least three months, and most preferably at least six months. For example, the Midkine family protein or the medicament may be used 1, 2, 3, 4, 5, 6 or 7 times per week, corresponding with one use per day that the Midkine family protein or medicament is applied. On any day, use of the Midkine family protein or medicament may correspond with application 1, 2, 3, 4 or 5 times per day. In one embodiment, the Midkine family protein or medicament is applied to the mammal once per day and three or five times per week.

Typically, a topical formulation comprising a Midkine family protein may be applied in the amount of 0.001 to 1,000 $\mu g/cm^2/day$, 0.005 to 500 $\mu g/cm^2/day$, 0.01 to 100 $\mu g/cm^2/day$, 0.05 to 50 $\mu g/cm^2/day$, or 0.1 to 10 $\mu g/cm^2/day$. Typically, the dose to be applied topically on the scalp is in the range of about 0.1 ng to about 100 mg per day, more preferably about 1 ng to about 10 mg per day, and most preferably about 10 ng to about 1 mg per day depending on the Midkine family protein(s) and the formulation. Typically, the daily amount of Midkine family protein(s) for treatment of the eyelid may be about 0.1 ng to about 100 mg per eyelid.

The Midkine family protein may be applied alone as an active ingredient, or may be applied with other active ingredients. Similarly, the medicament may comprise further active ingredients in addition to the Midkine family protein. Such active ingredients other than the Midkine family protein may be, but are not limited to, cellular stimulants, blood circulation promoting agents, anti-androgen drugs, sebum secretion suppressing agents, immunosuppressants, antihistamine agents, antimicrobials, focal stimulants, emollients, antiphlogistics, or low-molecular anti-apoptotic agents. Specifically, said other active ingredients may be at least one of pantothenic acid or variants thereof, placenta extract, photosensitizers, ginseng extract, biotin, mononitro guaiacol, carpronium chloride or hydrates thereof, vitamin E or variants thereof, *Swertia japonica* extract, *capsicum* tincture, cepharanthine, nicotinic acid or variants thereof, estradiol, ethynylestradiol, randic acid, minoxidil or analogs/variants thereof, 5α-reductase inhibitor, 12-tetradecanoylphorbol-13-acetate, herbal medicine such as *Polygonatum* rhizome, *Uncaria, Silybum marianum*, henna, and *Glycyrrhiza*, estradiol benzoate, diphenhydramine, resorcin, hinokitiol, 1-menthol, salicylic acid, *Polygonum* root extract, *Panax japonicus* rhizome extract, panthenol, selenium disulfide, pyridoxine hydrochloride, dipyrithione zinc, pyrithione zinc, sulfur, piroctone olamine, pyrithione zinc, sulfur, glycyrrhetinic acid stearyl, glycyrrhizinate dipotassium, allantoin, dialkylmonoamine variants, *Perilla frutescens* extract, *Poria sclerotium* extract, β-glycyrrhetinic acid, miconazole nitrate, benzoic acid, sodium salicylate, phytosterol, wine yeast extract, takanal, ethinyl estradiol, isopropylmethylphenol, cepharanthine biotin, D-pantothenyl alcohol, *Paeonia* extract, *Tilia* extract, *Sophora* extract, *Sophora flavescens* extract, *Zingiber Officinale* (Ginger) root extract, 6-benzylaminoprine, pentadecanoic glyceride, t-flavanone, sweet *Hydrangea* leaf extract, adenosine, and pantothenylethylether.

In one example, a formulation comprising a midkine family protein is administered sequentially or simultaneously with an adjunctive therapeutic agent for treatment of the same condition e.g., cestradiol and/or oxandrolone and/or minoxidil and/or finasteride or an agent that blocks the conversion of testosterone to dihydrotesterone. The adjunctive therapeutic agent is co-administered under conditions and in accordance to a standard treatment regime for that agent. The skilled artisan will appreciate that such treatment regimens provide enhanced therapeutic benefit to the patient, and may be more than additive in their effect.

Alternatively, or in addition, a formulation comprising a midkine family protein is administered sequentially or simultaneously with a cytotoxic or cytostatic compound that causes hair loss e.g., in the case of a subject undergoing chemotherapy or radiation therapy or treatment for HIV-1 infection or AIDS. In such circumstances, the efficacy of the midkine family protein counteracts the hair-loss effect of the cytotoxic or cytostatic compound. The cytotoxic or cytostatic compound will generally be administered in accordance to a standard treatment regime for that agent. Conveniently, the Midkine family protein and the cytotxin/cytostatin are administered via the same route e.g., parenterally.

Subjects

The compositions of the present invention are suitable for medical treatment of humans and other mammals, including treatment companion animals such as dogs and cats, and domestic animals such as horses, zoo animals such as felids, canids, bovids, ungulates and primates, or laboratory animals such as rodents, lagomorphs and primates. The compositions are particularly suitable for treatment of any mammal that suffers alopecia of any form, especially humans, primates dogs, cats, or horses.

The subject to be treated may be afflicted with hair thinning, hair loss or alopecia, or may not be afflicted with hair thinning, hair loss or alopecia (i.e., free of detectable disease), but is prone to develop hair thinning, hair loss or alopecia.

A Midkine family protein, or a medicament comprising a Midkine family protein, may be used to treat hair thinning, hair loss or alopecia caused by cytotoxic or cytostatic agents. The cytotoxic or cytostatic agents may be endogenous, e.g. as generated in response to stress, or may be exogenous, e.g. as administered during chemotherapy for treatment of cancer.

The present invention is particularly suited to treatment and prevention of alopecia in subjects that are either undergoing treatment with a cytotoxic or cytostatic compound described herein, or to whom such therapy has been prescribed. As exemplified herein, the subject may be treated before therapy with a cytotoxic or cytostatic compound commences, or before and after such therapy has commenced. The present invention also provides for commences of midkine family protein therapy after treatment with a cytotoxic or cytostatic compound has commenced.

For example, a subject may apply a composition described herein as a fine line at the skin-eyelash border of each eyelid, and as a cream to the scalp, once a day several weeks e.g., two weeks or three weeks, prior to the initiation of a chemotherapy regimen (e.g., doxorubicin, cyclophosphamide, and paclitaxel, or 5-fluoruracil, leucovorin and oxaliplatin). The patient may continue applying the composition throughout and after cessation of the chemotherapy regimen. The patient would not generally experience the total hair loss normally associated with chemotherapy, and may recover more rapidly when chemotherapy ceases. A few weeks after completion of the chemotherapy, the patient may stop applying the composition. If hair is lost at this stage, treatment is resumed.

The present invention is illustrated in detail below with references to examples, but is not to be construed as being limited thereto.

EXAMPLE 1

Method for Producing Recombinant Midkine

A cDNA fragment comprising human MK open reading frame (nucleotide positions 1-432; SEQ ID NO: 4) was inserted into the yeast expression vector pPIC9 (Invitrogen). This recombinant plasmid was transfected into yeast (*Pichia pastoris* GS115; Research Corporation Technologies), and the desired clones were selected with histidine and G418.

Human MK protein secreted by yeast into the culture medium was purified by employing the following column chromatography in the order below:
1. SP Steamlines (Pharmacia; adsorption and wash with 20 mM pH 5.5 acetate buffer, elution with 20 mM pH 3.5 acetate buffer containing NaCl);
2. Sulfated Cellulofine (Seikagaku Kogyo, Japan; adsorption with 10 mM pH 7.2 phosphate buffer, wash with buffer containing 0.7 M NaCl, elution with buffer containing 2.0 M NaCl);
3. Superdex 75 pg (Pharmacia; gel filtration with saline);
4. Poly. Sulfoethyl A (Poly LC Co.; adsorption with 20 mM buffer containing 0.6 M NaCl, wash with buffer containing 0.88 M NaCl, elution with buffer containing 2M NaCl); and
5. Superdex 75 pg (Pharmacia; gel filtration with saline).

The Midkine preparation was dialyzed against saline. The activity of purified MK protein was detected using as an index the activity of MK for promoting the survival of embryonic neurons.

EXAMPLE 2

Hair-growing effects of external applications of midkine (MK) and pleiotrophin (PTN) 1 μg/ml of MK or PTN in 40% glycerol/phosphate buffered saline (PBS) (v/v) was prepared. 10 μl of the solution of MK or PTN was directly applied three times per week to alopecic regions of aged Black 6 mice (1.5 years old, MK heterozygous knockout (+/−)). It was observed for 25 days after starting the application whether each of MK and PTN had a hair-growing effect. FIG. 1 shows the results of the observation. As clearly understood from FIG. 1 and the brief description thereof, application of MK or PTN promoted hair growth on the alopecic regions of the aged mice. In this experiment, the applications of MK and PTN stopped on Day 15, because the hair-growing effect of MK and PTN was already confirmed on Day 15, From Day 15 to Day 25, the amount of hair increased even though the applications of MK and PTN were stopped (FIG. 1). This shows that the hair-growing effects of MK and PTN last for some time even after their applications are stopped.

EXAMPLE 3

Hair-Growing Effects of Subcutaneous Injection of MK and PTN

Figure 2:
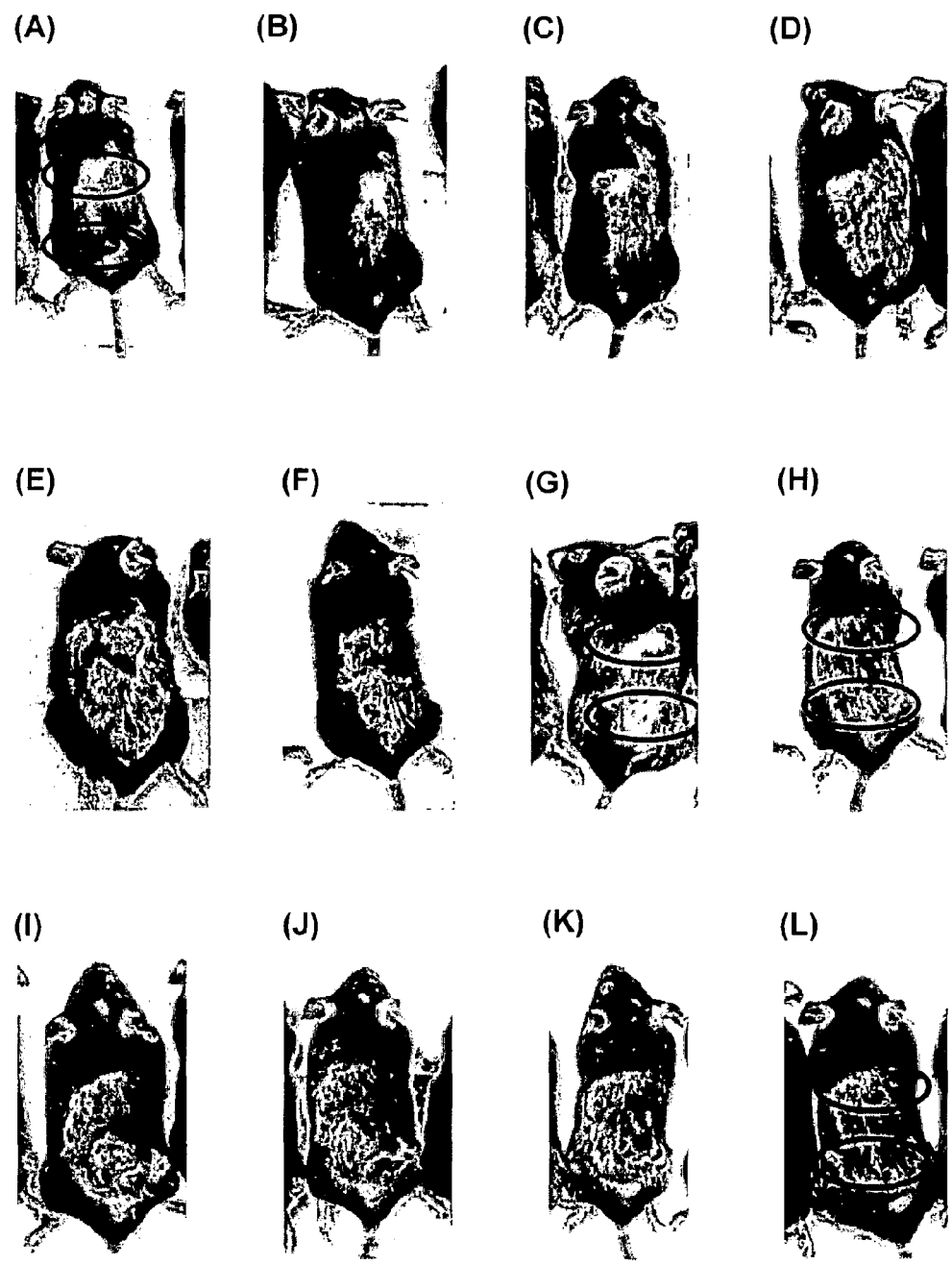
FIG. 2 provides photographic representations showing the effect of a parenteral, i.e., subcutaneous, formulations comprising MK (1 µg/ml) or 50 µl of PTN (1 µg/ml) to different alopecic regions of aged Black 6 MK homozygous knockout (−/−) mice at 1.5 years of age for 15 days, followed by treatment with topical formulations described in the legend to FIG. 1 for a further 10 days. In the drawing, the circles in each row indicate the positioning of subcutaneous injections and dermal patches of MK (circle nearer the neck region) and PTN (circles nearer the tail) for each animal in the same row. Panel A shows an animal on the day treatment was commenced. Panels B-L show mice at day 1, 4, 6, 8, 11, 13, 15, 18, 20, 22, and 25 respectively from commencement of treatment. Panel H shows an animal on the day that thrice-weekly topical treatment commenced. Data indicate that animals treated with a sub-cutaneous injection of MK or PTN showed no macroscopic signs of fur regrowth 15 days later. However, 10 days following commencement of topical therapy, administration of MK or PTN had stimulated fur growth in this animal model (panel L). Fur regrowth was not entirely localized to the treated region, since animals showed improved fur condition over their entire dorsal region following treatment.

1 μg/ml of MK or PTN in PBS was prepared. 50 μl of the solution of MK or PTN was injected subcutaneously into aged Black 6 mice (1.5 years old, MK homozygous knockout (−/−)). The subcutaneous injections of MK and PTN showed no hair-growing effect on Day 15 (FIG. 2) under these conditions in this animal model. After changing on Day 15 from the subcutaneous injection to external applications of MK or PTN in accordance with Example 2, the hair-growing effects of MK or PTN were observed on Day 25 (FIG. 2).

EXAMPLE 4

Hair-Growing Effect of Intravenous Injection of MK

1 μg/ml of MK in PBS was prepared. 100 μl of the solution of MK was injected intravenously into aged Black 6 mice (1.5 years old, MK homozygous knockout (−/−)). The intravenous injection of MK showed no hair-growing effect under these conditions and in this animal model (data not shown).

EXAMPLE 5

Hair-Growing Effects of External Applications of MK and PTN

Figure 3:
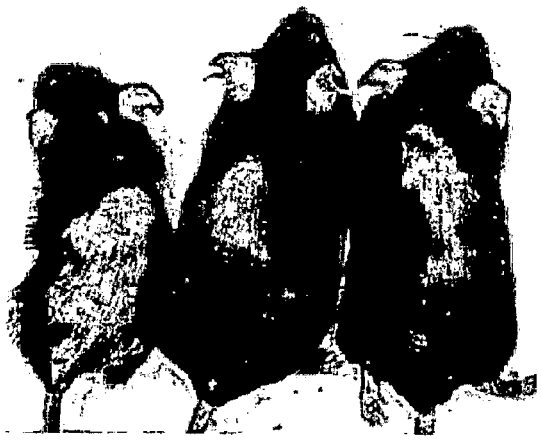
FIG. 3 provides photographic representations showing a fur-growth promoting effect of externally applying 100 µl of MK in 10% glycerol (2 µg/ml) five times per week to alopecic regions of Black 6 MK heterozygous knockout (+/−) mice at 1.5 years of age. Panel A shows animals on the day treatment was commenced. Panels B-F show mice at day 7, day 14, day 21, day 28, and day 35 respectively from commencement of treatment. Data show progressive fur regrowth during the 35 day test period, with significant fur regrowth evident after about 21-28 days (panels C and D).
Figure 3:
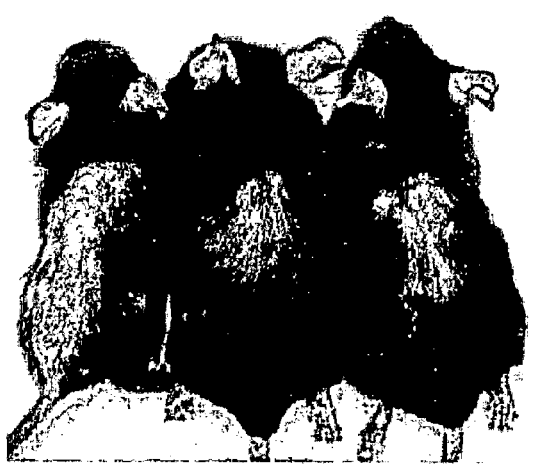
Figure 3:
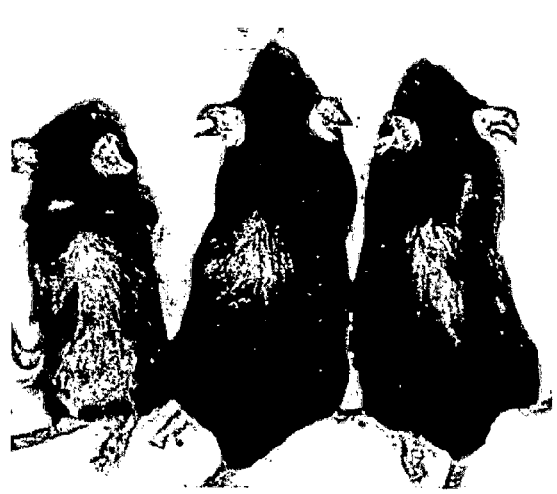
Figure 3:
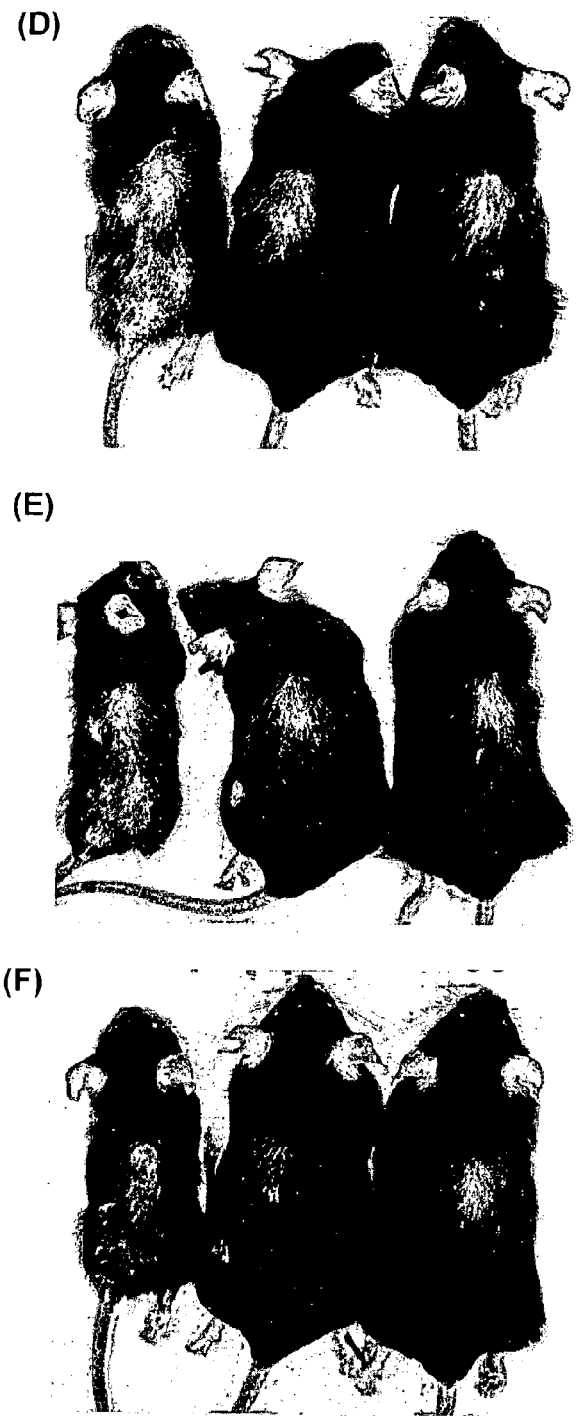
Figure 4:
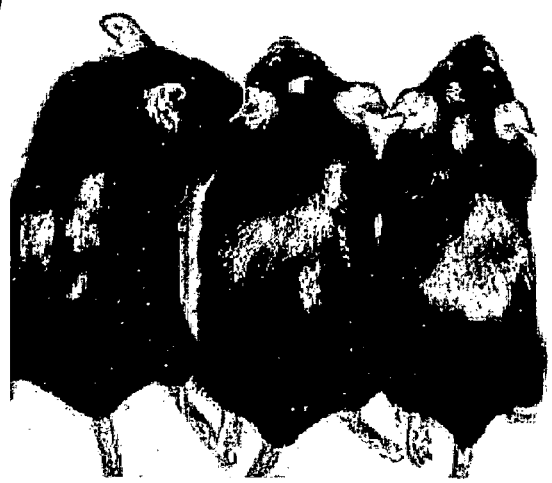
FIG. 4 provides photographic representations showing a fur-growth promoting effect of externally applying 100 µl of PTN in 10% glycerol (2 µg/ml) five times per week to alopecic regions of Black 6 MK heterozygous knockout (+/−) mice at 1.5 years of age. Panel A shows animals on the day treatment was commenced. Panels B-F show mice at day 7, day 14, day 21, day 28, and day 35 respectively from commencement of treatment. Data show progressive fur regrowth during the 35 day test period, with significant fur regrowth evident after about 21-28 days (panels C and D).
Figure 4:
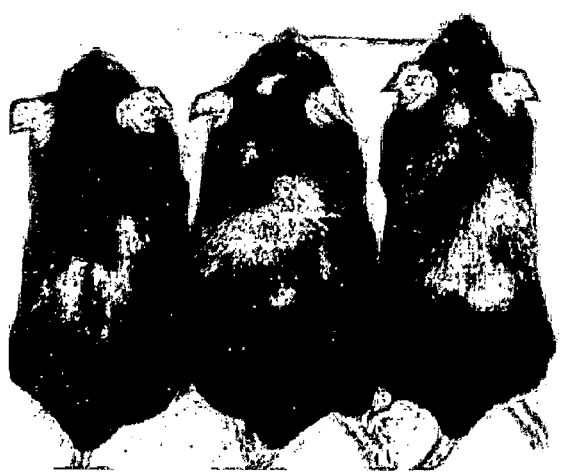
Figure 4:
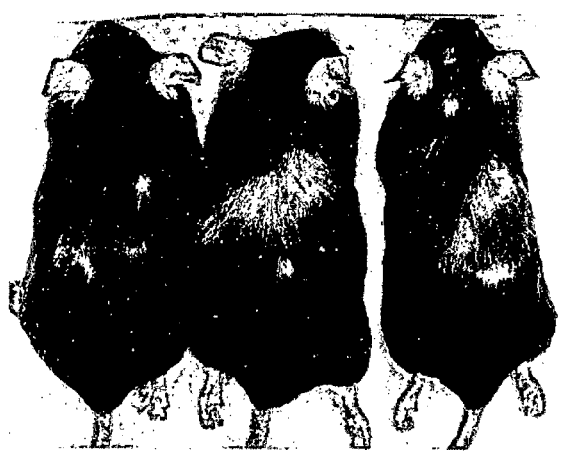
Figure 4:
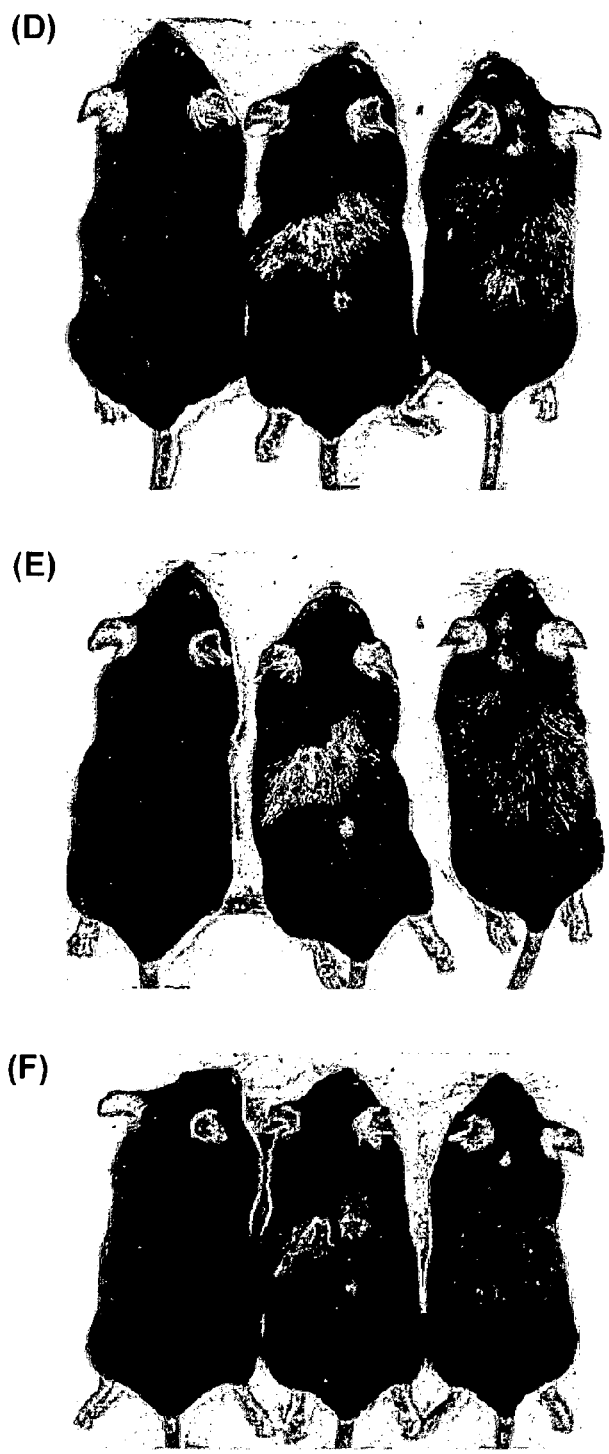
Figure 5:
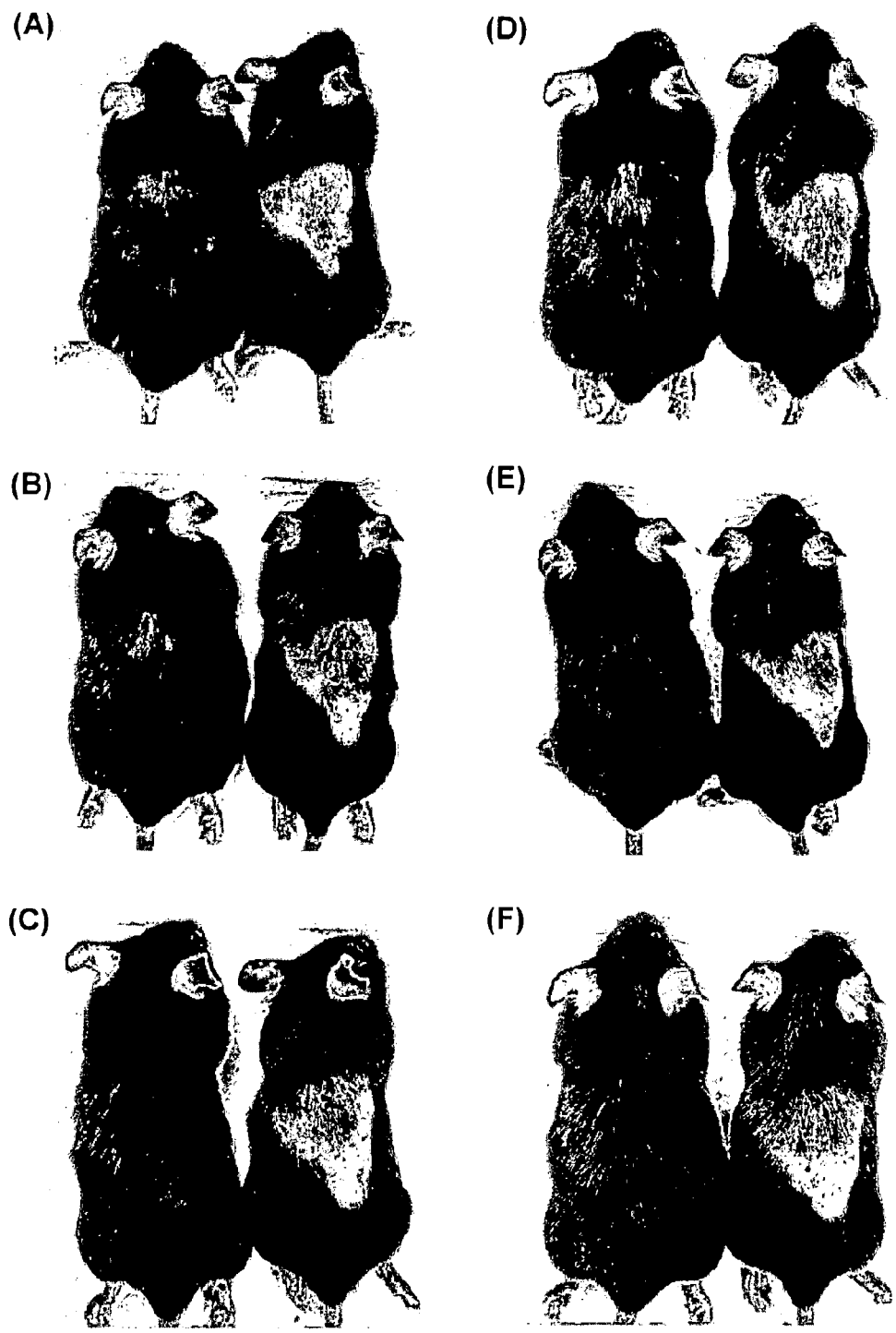
FIG. 5 provides photographic representations showing the fur-growth promoting effect of externally applying 100 µl of minoxidil (RiUP®, Taisho Pharmaceutical Co., Ltd.) to alopecic regions of aged Black 6 MK heterozygous knockout (+/−) mice as a positive control to the experiments of FIGS. 3 and 4. Panel A shows animals on the day treatment was commenced. Panels B-F show mice at day 7, day 14, day 21, day 28, and day 35 respectively from commencement of treatment. Data show less effective treatment with minoxidil than that observed following treatment with MK or PTN because substantial areas of skin failed to regrow fur after 35 days treatment with minoxidil.

2 μg/ml of MK or PTN in 10% glycerol/PBS (v/v) was prepared. 100 μl of the solution of MK or PTN was applied directly five times per week to alopecic regions of aged Black 6 mice (1.5 years old, MK heterozygous knockout (+/−)). It was observed for 35 days after starting the application whether each of MK and PTN had a hair-growing effect. FIGS. 3 and 4 show the results of the observation. Minoxidil (e.g., 1% w/v; RiUP®, Taisho Pharmaceutical Co., Ltd.) was used as a positive control (FIG. 5). As clearly understood from FIGS. 3 and 4 and the brief descriptions thereof, both applications of MK and PTN under these conditions showed hair-growing effects on the alopecic regions of the aged mice.

EXAMPLE 6

Figure 6:
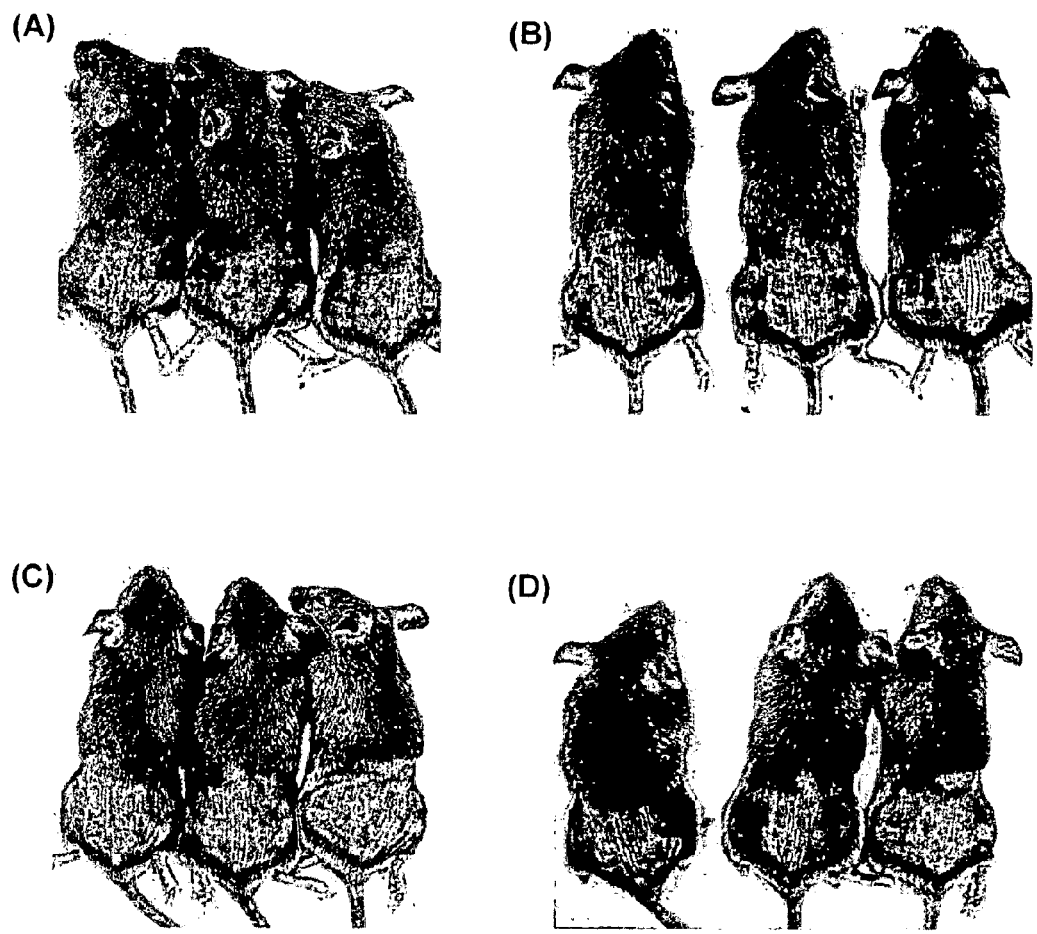
FIG. 6 provides photographic representations showing fur regrowth in shaved regions of nine-week old male C3H/HeJ mice following external application of 100 µl of 10% (v/v) glycerol/phosphate buffered saline (PBS) as a negative control for the experiments of FIGS. 8 and 9. Panel A shows animals on the day treatment was commenced. Panels B-D show mice at day 7, day 14, and day 21 respectively from commencement of treatment. Data show slow fur regrowth which becomes apparent macroscopically only on about day 21.
Figure 7:
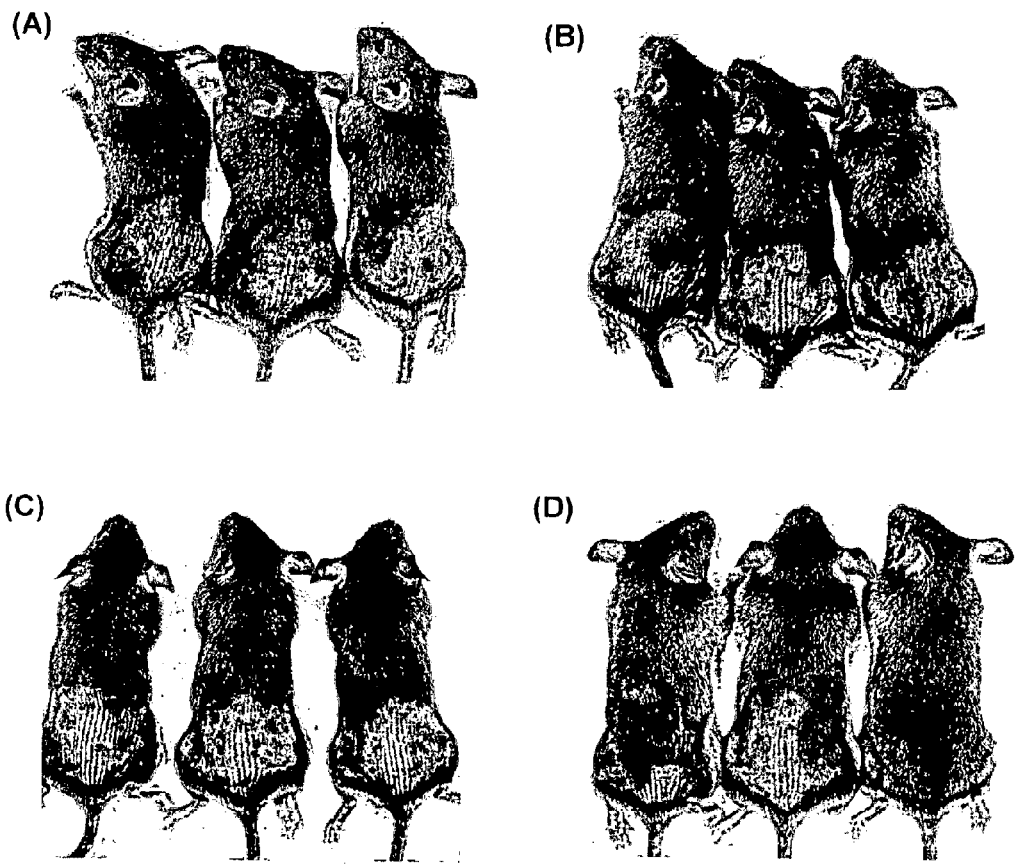
FIG. 7 provides photographic representations showing fur regrowth in shaved regions of nine-week old male C3H/HeJ mice following external application of 100 µl of minoxidil (e.g., 1% w/v; RiUP®, Taisho Pharmaceutical Co., Ltd.) as a positive control for the experiments of FIGS. 8 and 9. Panel A shows animals on the day treatment was commenced. Panels B-D show mice at day 7, day 14, and day 21 respectively from commencement of treatment. Data show slow fur re-growth which becomes apparent macroscopically only on about day 21, consistent with the vasodilatory effect of minoxidil on dermal papillae.
Figure 8:
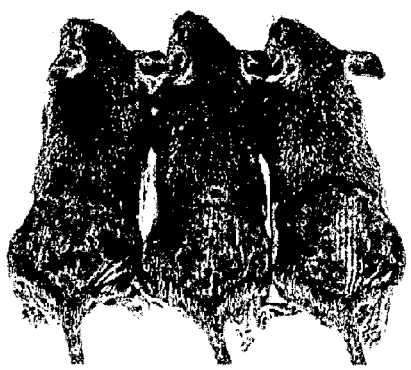
FIG. 8 provides photographic representations showing fur regrowth in shaved regions of nine-week old male C3H/HeJ mice following external application of 100 µl of MK in 10% glycerol/PBS (2 µg/ml). Panel A shows animals on the day treatment was commenced. Panels B-D show mice at day 7, day 14, and day 21 respectively from commencement of treatment. Data show slow fur regrowth which becomes apparent macroscopically only on about day 21, suggesting a different mode of action for MK to minoxidil in animals that have merely been synchronized in the anagen phase, without exhibiting symptoms of alopecia.
Figure 8:
Figure 8:
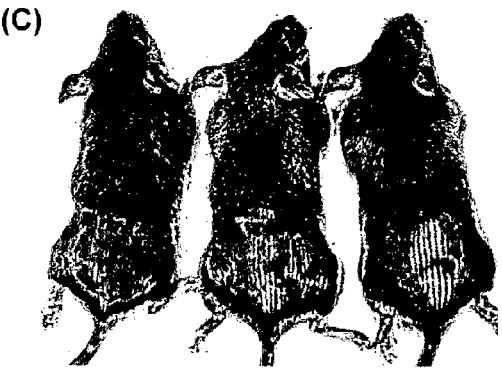
Figure 8:
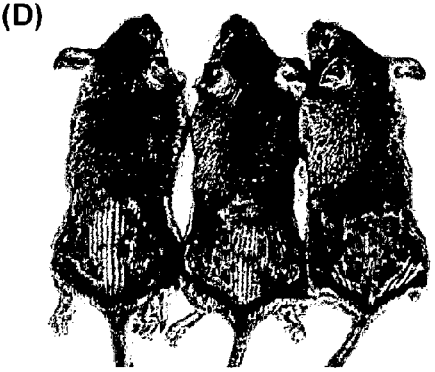
Figure 9:
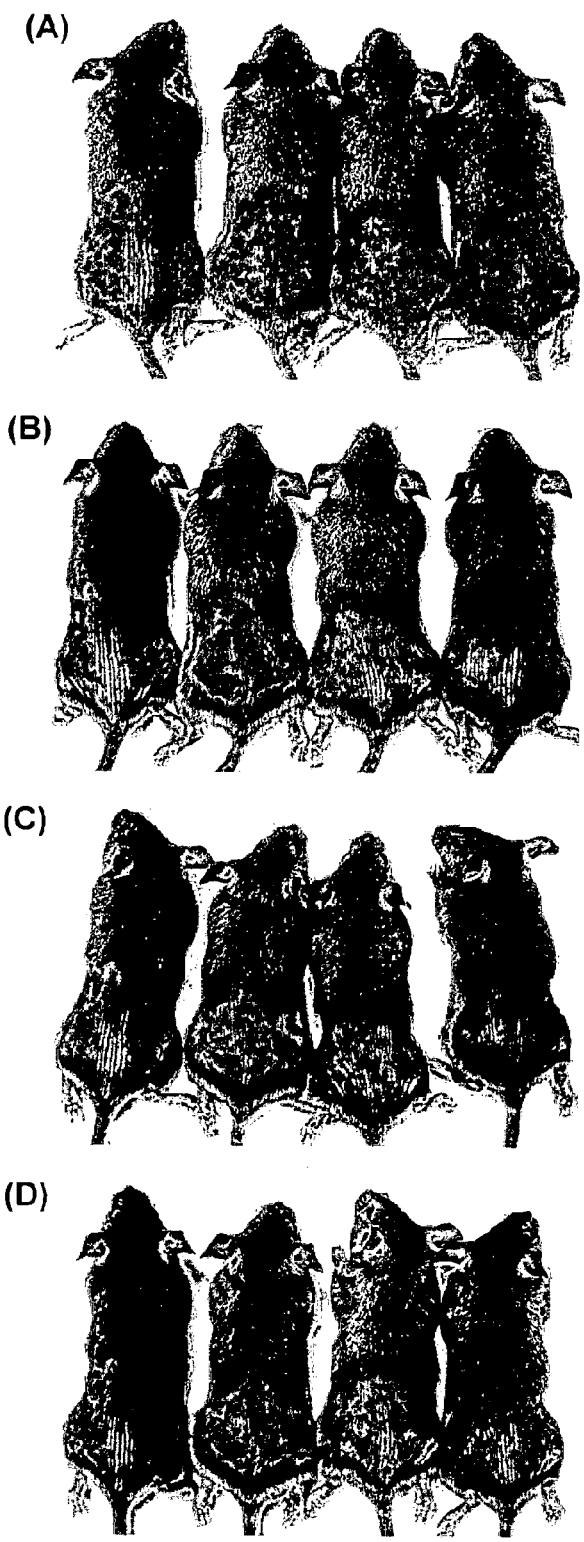
FIG. 9 provides photographic representations showing fur regrowth in shaved regions of nine-week old male C3H/HeJ mice following external application of 100 µl of PTN in 10% glycerol/PBS (2 µg/ml). Panel A shows animals on the day treatment was commenced. Panels B-D show mice at day 7, day 14, and day 21 respectively from commencement of treatment. Data show slow fur regrowth which becomes apparent macroscopically only on about day 21, suggesting a different mode of action for MK to minoxidil in animals that have merely been synchronized in the anagen phase, without exhibiting symptoms of alopecia FIG. 10 provides a graphical representation showing the percentage alopecia developed in a murine model of cyclophosphamide-induced alopecia over time (days) following synchronization in anagen phase by shaving and waxing on day 1, and 150 mg/kg cyclophosphamide (CYP) injection i/p on day 9. Percentage alopecia was determined as the percentage of the area of skin to which the dermal patches were applied showing fur loss on the indicated day of measurement. Circles show alopecia in animals receiving daily saline placebo i.e., without midkine protein, in addition to CYP. Filled squares (MK 2-29) show percentage alopecia in animals receiving 5 µg midkine protein topically on a daily basis from day 2 to day 29 when the experiment was terminated. Filled triangles (MK-10-29) show percentage alopecia in animals receiving 5 µg midkine protein each on a daily basis from day 10 to day 29 when the experiment was terminated. Data demonstrate that midkine protein reduces CYP-induced fur loss when administered before and/or following CYP, and that midkine increases a rate of follicle recovery as determined by fur growth following cessation of CYP treatment. Under these conditions, maximum differentiation between animals receiving the placebo control and animals receiving midkine was detectable on days 12-14.
Figure 10:
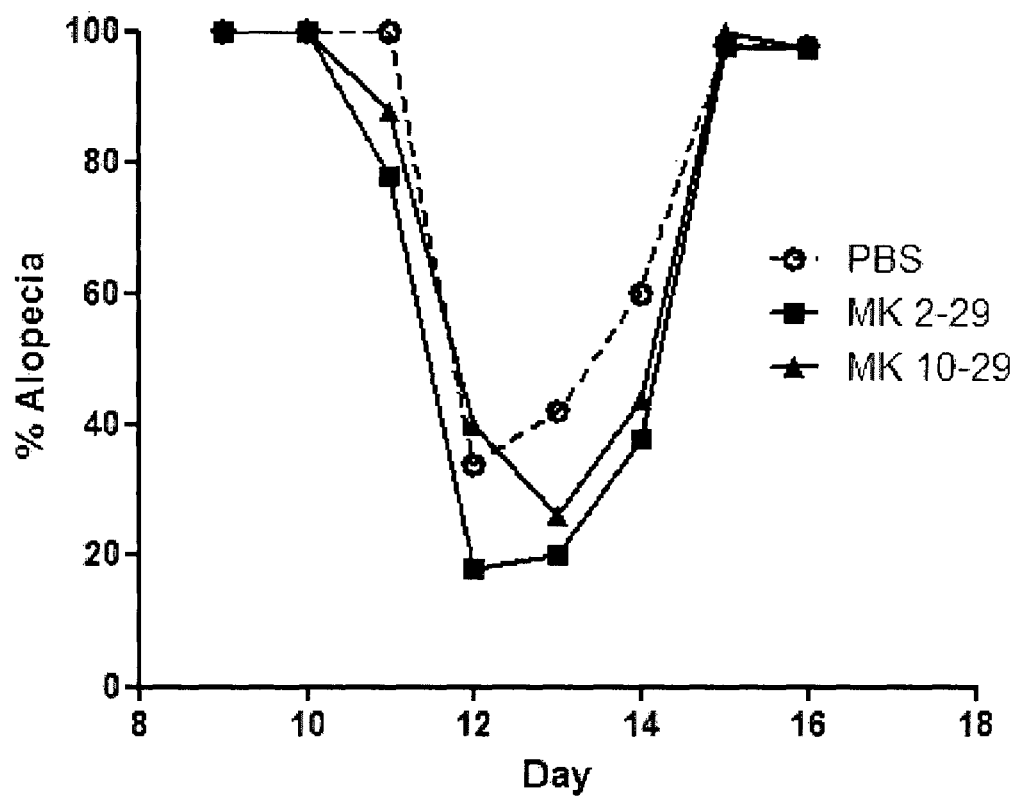

Hair-Growing Effects of External Applications of MK and PTN are Different to the Effect of Minoxidil 2 μg/ml of MK or PTN in 10% glycerol/PBS (v/v) was prepared. 100 μl of the solution of MK or PTN was applied directly to shaved regions of C3H/HeJ mice (male, nine weeks old). 10% glycerol/PBS (v/v) and minoxidil (e.g., 1% w/v; RiUP®, Taisho Pharmaceutical Co., Ltd.) were used as negative and positive controls, respectively (FIGS. 6 and 7). It was observed for 21 days after starting the application whether each of MK and PTN showed enhancement of hair growth in the anagen phase. FIGS. 8 and 9 show the results of the observation. The application of minoxidil (RiUP®) showed enhancement of hair growth (FIG. 7). In contrast, MK and PTN showed no such enhancement (FIGS. 8 and 9). The available data suggest a different mode of action for MK to minoxidil in animals that have merely been synchronized in the anagen phase, without exhibiting symptoms of alopecia.

EXAMPLE 7

Effect of External Application of MK on Acute Alopecia

Animal Ethics

All procedures were approved by the Royal Melbourne Institute of Technology (RMIT) Animal Experimentation and Ethics Committee (AEEC Project #1042), Melbourne, Australia.

Animals

A total of thirty-five mice were used in the study.

Pathogen-free female C57Bl/6J mice were obtained from Animal Resource Centre, Canning Vale, Western Australia, Australia. Animals were housed under standard clean conventional animal house conditions in a single room within the RDDT Animal Facility (201.01), maintained at target values of 22±2° C. and 30-70% relative humidity, with a 12 h light:dark cycle. Animals were fed irradiated Rat and Mouse Chow (Specialty Feeds, Glen Forrest, Western Australia, Australia) and supplied municipal town water ad libitum. Fresh water was supplied at least twice weekly. Periodic testing of feed, bedding and water was undertaken to identify any contaminants that might interfere with the study results.

Animals were randomised into study groups, housed in groups of two to three per cage and subjected to at least a two-day quarantine period on receipt. The animals were identified by implantation of microchip transponders by sub-cutaneous injection between the shoulder blades. Secondary identification of animals within each cage was made by use of tail markings with a permanent marker. Mice were housed individually prior to the commencement of treatment if there appeared to be excessive grooming of depilated mouse skin by cage-mates.

As the commencement of treatment, mice were aged between five weeks and seven weeks, and varied in weight by no more than 20% of their mean weight.

Induction of Acute Alopecia

Acute alopecia was induced according to the procedures described by Paus et al., *Am. J. Pathol.* 144, 719-734 (1994), i.e., by a single intraperitoneal injection of cyclophosphamide to C57 BL/6 mice. The study includes 35 female C57Bl/6J mice divided into seven experimental groups of five mice each as outlined in the text table below:

| | Cyclophosphamide | | Midkine Treatment | | No. of |
|---|---|---|---|---|---|
| Group | mg/kg | Study Day | μg/mL | Study Day | animals |
| 1 | 0 | 9 | 0 | 2-29 | 5 |
| 2 | 50 | 9 | 0 | 2-29 | 5 |
| 3 | 50 | 9 | 10 | 2-29 | 5 |
| 4 | 50 | 9 | 10 | 10-29 | 5 |
| 5 | 150 | 9 | 0 | 2-29 | 5 |
| 6 | 150 | 9 | 10 | 2-29 | 5 |
| 7 | 150 | 9 | 10 | 10-29 | 5 |

The following protocol was employed:

Study Day 1: Mice were anaesthetized by intraperitoneal injection with a combination of ketamine (50 mg/kg), xylazine (5 mg/kg) and acepromazine (0.8 mg/kg). Fur was removed from a test area of approximately 2×4 cm on the backs of the mice, by shaving with an electric clipper. The skin was rinsed with warm water to clean the area and patted dry. The remaining fur was removed by use of a commercial hair remover wax strip.

Study Days 2-9: Mice in groups 1, 2, 3, 5 and 6 were administered a final dose concentration of 5 μg midkine/mouse/day, or a control phosphate buffered saline (PBS) solution, by dermal application to the test area in a volume of 0.5 mL. Mice in groups 4 and 7 were administered a control phosphate buffered saline (PBS) solution, by dermal application to the test area in a volume of 0.5 mL.

Study Day 9: Mice in all groups were treated with either vehicle (water) or cyclophosphamide by intraperitoneal injection in a dose volume of 10 mL/kg.

Study Days 10-29: Mice in groups 4 and 7 were administered a final dose concentration of 5 μg midkine/mouse/day, by dermal application to the test area in a volume of 0.5 mL. Mice in groups 1, 2, 3, 5 and 6 were administered a final dose concentration of 5 μg midkine/mouse/day, or a control phosphate buffered saline (PBS) solution, by dermal application to the test area in a volume of 0.5 mL. Animals in groups 1, 2, 3, 5, and 6 that received the control solution on days 2-9 also received the control solution on days 10-29. Animals in groups 1, 2, 3, 5, and 6 that received the midkine solution on days 2-9 also received the midkine solution on days 10-29.

Study Day 30: Mice were sacrificed by exposure to a rising concentration of carbon dioxide. A portion of skin in the target area was collected and preserved in 10% neutral buffered formalin for macroscopic and microscopic examination.

Mice were monitored daily from Study Day 1-29 for clinical signs of toxicity. These observations will include assessment of any changes in the following:

Skin and fur (roughness, piloerection, lack of grooming, fur loss);
Eyes and mucous membranes (discharge, cloudiness, sores around eyes);
Respiratory, circulatory, autonomic or central nervous system functions;
Somatomotor activity and behaviour patterns (check for abnormal posture, gait and any abnormal activity);
Any tremors, convulsions, salivation, diarrhoea, lethargy, excessive sleeping or coma.

Skin/Fur Observations

From Study Day 9-29 onwards, mice were observed daily for signs of alopecia (fur loss) and changes in skin colour pigmentation. The degree of fur loss was determined as a percentage of target area with alopecia (fur loss), and skin pigmentation was scored as black, grey or pink. Group incidence findings for alopecia and skin pigmentation changes were determined for control and test groups by One-Way Analysis of Variance tests using GraphPad Prism 5.0 for Windows, GraphPad Software, San Diego Calif. USA.

The extent of fur loss/re-growth was also documented by twice-weekly photographs. To facilitate the photography process, the mice were sedated using ketamine (50 mg/kg), xylazine (5 mg/kg), acepromazine (0.8 mg/kg) anaesthetic.

Terminal Measurements

Skin samples were collected from the target area of each animal and preserved in 10% neutral buffered formalin for histopathological assessment.

Figure 11:
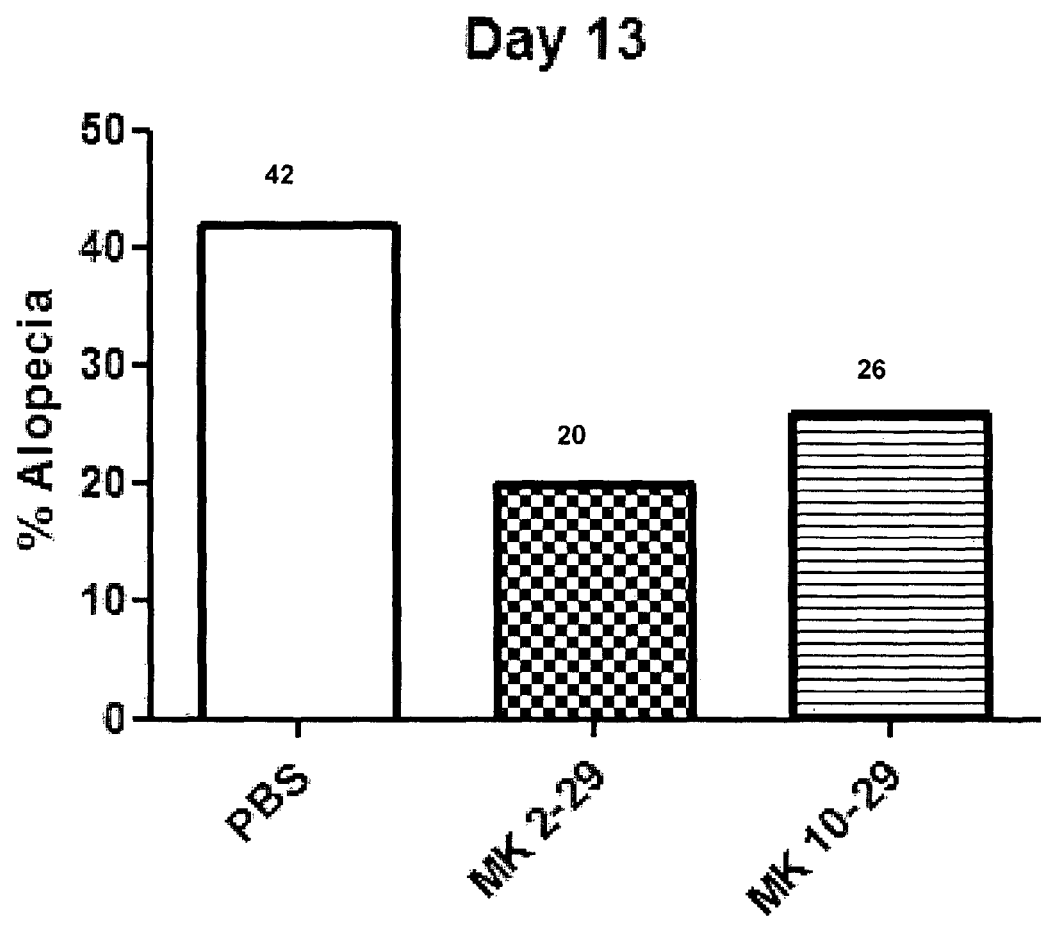
FIG. 11 provides a graphical representation of the percentage alopecia on day 13 of the data presented in FIG. 10. Percentage alopecia was determined as the percentage of the area of skin to which the dermal patches were applied showing fur loss on the indicated day of measurement. The open bar (PBS) shows 42% alopecia in animals receiving daily saline placebo i.e., without midkine protein, in addition to CYP. The hatched bar (MK 2-29) show only 20% alopecia in animals receiving 5 µg midkine protein topically on a daily basis from day 2 to day 29 when the experiment was terminated. The striped bar (MK-10-29) shows only 26% alopecia in animals receiving 5 µg midkine protein each on a daily basis from day 10 to day 29 when the experiment was terminated. Data demonstrate that midkine protein reduces CYP-induced fur loss when administered before and/or following CYP, and that midkine increases a rate of follicle recovery as determined by fur growth following cessation of CYP treatment.
Figure 12:
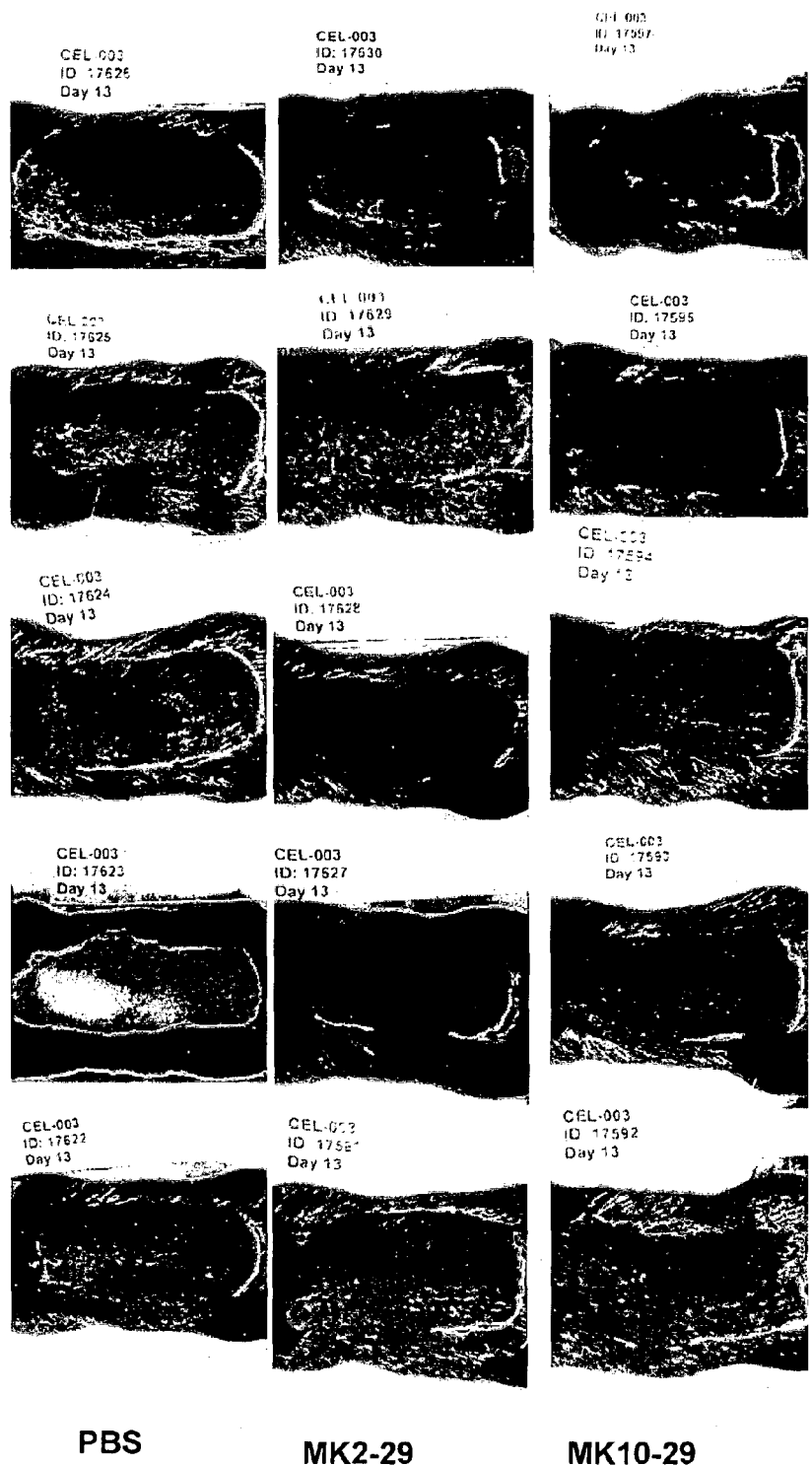
FIG. 12 provides photographic representations of the back skin of 15 mice, each treated with phosphate buffered saline placebo i.e., without midkine protein, administered daily as a topical formulation (group of 5 mice labeled PBS), or 5 µg midkine protein administered daily as a topical formulation before and/or after receiving a single cyclophosphamide (CYP) injection i/p (group of 5 mice labeled MK 2-29), or treated topically with 5 µg midkine protein on a daily basis after receiving a single 150 mg/kg cyclophosphamide (CYP) injection i/p (group of 5 mice labeled MK 10-29). Animals were observed for signs of fur regrowth/alopecia and skin pigmentation. Data indicate that mice treated with PBS exhibit extensive fur loss and grey or pink skin colour, especially in their neck regions, consistent with a predominance of follicles in catagen (grey) or telogen (pink). Mice treated with midkine protein before and after CYP treatment (MK2-29) showed reduced areas of fur loss relative to the group receiving PBS, and skin was either uniformly black or dark grey in color consistent with a predominance of follicles in anagen (black) and a lower proportion in catagen. Almost no pink skin was evident in this group, suggesting a much reduced proportion of follicles in telogen. Similarly, mice treated with midkine protein only following CYP treatment (MK10-29) showed reduced areas of fur loss relative to the group receiving PBS, and appeared macroscopically similar to animals receiving midkine protein before and after chemotherapy. The skin of mice receiving midkine protein only after chemotherapy was uniformly dark grey in color, consistent with a predominance of follicles in anagen or catagen.

Data in FIG. 11 demonstrate that midkine protein reduces cyclophosphamide-induced fur loss when administered before and/or following cyclophosphamide, and that midkine increases a rate of follicle recovery as determined by fur growth following cessation of cyclophosphamide treatment. Data in FIG. 12 indicate that mice treated with PBS exhibit extensive fur loss and grey or pink skin colour, especially in their neck regions, consistent with a predominance of follicles in catagen (grey) or telogen (pink). Mice treated with midkine protein before and after CYP treatment (MK2-29) showed reduced areas of fur loss relative to the group receiving PBS, and skin was either uniformly black or dark grey in color consistent with a predominance of follicles in anagen (black) and a lower proportion in catagen. Almost no pink skin was evident in this group, suggesting a much reduced proportion of follicles in telogen. Similarly, mice treated with midkine protein only following CYP treatment (MK10-29) showed reduced areas of fur loss relative to the group receiving PBS, and appeared macroscopically similar to animals receiving midkine protein before and after chemotherapy. The skin of mice receiving midkine protein only after chemotherapy was uniformly dark grey in color, consistent with a predominance of follicles in anagen or catagen.

We claim:

1. A method of treatment or prevention of hair loss, said method comprising: administering to a subject in need thereof an effective amount of a topical formulation comprising midkine to an affected area of skin of the subject in which hair has been lost or to an area of skin from which hair is likely to be lost, wherein said administering results in hair growth and/or reduction of hair loss.

2. The method according to claim 1, wherein the subject has alopecia.

3. The method according to claim 1, wherein the subject is susceptible to developing alopecia.

4. The method according to claim 2, wherein the alopecia is an acute form of alopecia.

5. The method according to claim 4, wherein the subject is undergoing treatment with a cytotoxic agent or cytostatic agent or has been prescribed treatment with a cytostoxic agent or cytostatic agent.

6. The method according to claim 2, wherein the alopecia is androgenic alopecia.

7. A method of reducing hair ioss in a subject undergoing chemotherapy or to whom chemotherapy has been prescribed, said method comprising: administering to the subject an effective amount of a topical formulation comprising midkine to an affected area of skin of the subject in which hair has been lost or to an area of skin from which hair is likely to be lost, wherein said administering results in hair growth and/or reduction of hair loss in the subject.

8. The method according to claim 7, wherein the subject has been treated with the chemotherapy.

9. The method according to claim 7, wherein the method comprises administering the midkine topically to a subject to whom chemotherapy has been prescribed before commencement of the chemotherapy.

10. The method according to claim 7, wherein the method comprises administering the midkine topically to the subject before and after commencement of the chemotherapy.

* * * * *

UNITED STATES PATENT AND TRADEMARK OFFICE
CERTIFICATE OF CORRECTION

| | |
|---|---|
| PATENT NO. | : 9,622,955 B2 |
| APPLICATION NO. | : 14/464358 |
| DATED | : April 18, 2017 |
| INVENTOR(S) | : Sadatoshi Sakuma et al. |

It is certified that error appears in the above-identified patent and that said Letters Patent is hereby corrected as shown below:

In the Claims

Column 36, Line 36, Claim 7 replace "ioss" with –loss–

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 4

<210> SEQ ID NO 1
<211> LENGTH: 143
<212> TYPE: PRT
<213> ORGANISM: Homo sapiens

<400> SEQUENCE: 1

Met Gln His Arg Gly Phe Leu Leu Leu Thr Leu Leu Ala Leu Leu Ala
1               5                   10                  15

Leu Thr Ser Ala Val Ala Lys Lys Asp Lys Val Lys Lys Gly Gly
            20                  25                  30

Pro Gly Ser Glu Cys Ala Glu Trp Ala Trp Gly Pro Cys Thr Pro Ser
        35                  40                  45

Ser Lys Asp Cys Gly Val Gly Phe Arg Glu Gly Thr Cys Gly Ala Gln
    50                  55                  60

Thr Gln Arg Ile Arg Cys Arg Val Pro Cys Asn Trp Lys Lys Glu Phe
65                  70                  75                  80

Gly Ala Asp Cys Lys Tyr Lys Phe Glu Asn Trp Gly Ala Cys Asp Gly
```

```
                85                  90                  95
Gly Thr Gly Thr Lys Val Arg Gln Gly Thr Leu Lys Lys Ala Arg Tyr
            100                 105                 110

Asn Ala Gln Cys Gln Glu Thr Ile Arg Val Thr Lys Pro Cys Thr Pro
            115                 120                 125

Lys Thr Lys Ala Lys Ala Lys Ala Lys Lys Gly Lys Gly Lys Asp
        130                 135                 140

<210> SEQ ID NO 2
<211> LENGTH: 168
<212> TYPE: PRT
<213> ORGANISM: Homo sapiens

<400> SEQUENCE: 2

Met Gln Ala Gln Gln Tyr Gln Gln Arg Arg Lys Phe Ala Ala Ala
1               5                   10                  15

Phe Leu Ala Phe Ile Phe Ile Leu Ala Ala Val Asp Thr Ala Glu Ala
            20                  25                  30

Gly Lys Lys Glu Lys Pro Glu Lys Val Lys Lys Ser Asp Cys Gly
        35                  40                  45

Glu Trp Gln Trp Ser Val Cys Val Pro Thr Ser Gly Asp Cys Gly Leu
50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
            115                 120                 125

Ala Glu Cys Gln Lys Thr Val Thr Ile Ser Lys Pro Cys Gly Lys Leu
        130                 135                 140

Thr Lys Pro Lys Pro Gln Ala Glu Ser Lys Lys Lys Lys Glu Gly
145                 150                 155                 160

Lys Lys Gln Glu Lys Met Leu Asp
                165

<210> SEQ ID NO 3
<211> LENGTH: 156
<212> TYPE: PRT
<213> ORGANISM: Homo sapiens

<400> SEQUENCE: 3

Met Gln His Arg Gly Phe Leu Leu Leu Thr Leu Leu Ala Leu Leu Ala
1               5                   10                  15

Leu Thr Ser Ala Val Ala Lys Lys Lys Asp Lys Val Lys Lys Gly Gly
            20                  25                  30

Pro Gly Ser Glu Cys Ala Glu Trp Ala Trp Gly Pro Cys Thr Pro Ser
        35                  40                  45

Ser Lys Asp Cys Gly Val Gly Phe Arg Glu Gly Thr Cys Gly Ala Gln
        50                  55                  60

Thr Gln Arg Ile Arg Cys Arg Val Pro Cys Asn Trp Lys Lys Glu Phe
65                  70                  75                  80

Gly Ala Asp Cys Lys Tyr Lys Phe Glu Asn Trp Gly Ala Cys Asp Gly
                85                  90                  95

Gly Thr Gly Thr Lys Val Arg Gln Gly Thr Leu Lys Lys Ala Arg Tyr
```

```
                     100                 105                 110
Asn Ala Gln Cys Gln Glu Thr Ile Arg Val Thr Lys Pro Cys Thr Pro
                 115                 120                 125

Lys Thr Lys Ala Lys Ala Lys Gly Gln Arg Lys Glu Lys Gly Val Gly
         130                 135                 140

Leu Ser Arg Gly Ala Ala Pro Pro Pro Arg Leu
145                 150                 155

<210> SEQ ID NO 4
<211> LENGTH: 562
<212> TYPE: DNA
<213> ORGANISM: Homo sapiens

<400> SEQUENCE: 4
atgcagcacc gaggcttcct cctcctcacc ctcctcgccc tgctggcgct caccteegeg    60 gtcgccaaaa agaaagataa ggtgaagaag ggcggcccgg ggagcgagtg cgctgagtgg   120
gcctgggggc cctgcacccc cagcagcaag gattgcggcg tgggtttccg cgagggcacc   180
tgcgggggcc agacccagcg catccggtgc agggtgccct gcaactggaa gaaggagttt   240
ggagccgact gcaagtacaa gtttgagaac tggggtgcgt gtgatggggg cacaggcacc   300
aaagtccgcc aaggcaccct gaagaaggcg cgctacaatg ctcagtgcca ggagaccatc   360
cgcgtcacca agccctgcac ccccaagacc aaagcaaagg ccaaagccaa gaaagggaag   420
ggaaaggact agacgccaag cctggatgcc aaggagcccc tggtgtcaca tggggcctgg   480
cccacgccct ccctctccca ggcccgagat gtgacccacc agtgccttct gtctgctcgt   540
tagctttaat caatcatgcc cc                                            562
```